(12) United States Patent
Serina et al.

(10) Patent No.: US 9,861,350 B2
(45) Date of Patent: Jan. 9, 2018

(54) DEVICES AND METHODS FOR ANCHORING TISSUE

(75) Inventors: Eugene Serina, Fremont, CA (US); Tammy Y. Tam, San Francisco, CA (US); Jennifer L. Henderson, Sunnyvale, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 0 days.

(21) Appl. No.: 13/820,447

(22) PCT Filed: Sep. 2, 2011

(86) PCT No.: PCT/US2011/050331
§ 371 (c)(1),
(2), (4) Date: Oct. 18, 2013

(87) PCT Pub. No.: WO2012/031204
PCT Pub. Date: Mar. 8, 2012

(65) Prior Publication Data
US 2014/0148849 A1    May 29, 2014

Related U.S. Application Data

(60) Provisional application No. 61/380,182, filed on Sep. 3, 2010.

(51) Int. Cl.
*A61B 17/04*   (2006.01)
*A61B 17/064*  (2006.01)
(Continued)

(52) U.S. Cl.
CPC .......... *A61B 17/0401* (2013.01); *A61B 5/686* (2013.01); *A61B 17/068* (2013.01);
(Continued)

(58) Field of Classification Search
CPC ............ A61B 17/0401; A61B 17/0644; A61F 2/2442
(Continued)

(56) References Cited

U.S. PATENT DOCUMENTS 2,108,206 A    2/1938  Meeker
3,656,185 A    4/1972  Carpentier
(Continued)

FOREIGN PATENT DOCUMENTS

EP    0 363 661 A1    4/1990
EP    0 669 101 A1    8/1995
(Continued)

OTHER PUBLICATIONS

International Search Report dated Feb. 21, 2012, for PCT Patent Application No. PCT/US2011/050331, filed on Sep. 2, 2011, 4 pages.
(Continued)

*Primary Examiner* — Diane Yabut
(74) *Attorney, Agent, or Firm* — Cooley LLP

(57) ABSTRACT

Described herein are devices and methods for delivering implants that have multiple coupled anchors. The anchors have an elongate form following a curved arcuate path in a single turning direction. Each anchor has two legs arranged to diverge away from each other, where each leg has a substantially non-constant radius of curvature and a substantially straight distal tip. The anchors are secured to tissue using a multi-opening guide tunnel that is configured to releasably retain one or more portions of the implant located between two of the anchors. The releasable retention of one or more intervening portions of the implant maintains the position of the implant and the guide tunnel until the implant is secured to the tissue. One variation of a multi-opening guide tunnel has releasable retention flaps and an aperture
(Continued)

capable of deploying a fluid contrast medium into a patient without interfering with anchor delivery.

4 Claims, 17 Drawing Sheets

(51) Int. Cl.
    *A61B 17/068*     (2006.01)
    *A61B 5/00*     (2006.01)
    *A61B 17/34*     (2006.01)
    *A61B 18/14*     (2006.01)
    *A61B 17/00*     (2006.01)
    *A61B 17/22*     (2006.01)
    *A61F 2/24*     (2006.01)
    *A61M 25/04*     (2006.01)
    *A61N 1/05*     (2006.01)
    *A61B 90/00*     (2016.01)

(52) U.S. Cl.
    CPC ........ *A61B 17/0644* (2013.01); *A61B 5/0002* (2013.01); *A61B 5/6877* (2013.01); *A61B 5/6882* (2013.01); *A61B 17/3478* (2013.01); *A61B 18/14* (2013.01); *A61B 2017/00022* (2013.01); *A61B 2017/00039* (2013.01); *A61B 2017/00044* (2013.01); *A61B 2017/00221* (2013.01); *A61B 2017/00305* (2013.01); *A61B 2017/00849* (2013.01); *A61B 2017/00858* (2013.01); *A61B 2017/00862* (2013.01); *A61B 2017/00867* (2013.01); *A61B 2017/00893* (2013.01); *A61B 2017/0409* (2013.01); *A61B 2017/0417* (2013.01); *A61B 2017/0427* (2013.01); *A61B 2017/0464* (2013.01); *A61B 2017/0649* (2013.01); *A61B 2017/22038* (2013.01); *A61B 2090/3904* (2016.02); *A61B 2090/3966* (2016.02); *A61F 2/2442* (2013.01); *A61M 25/04* (2013.01); *A61N 1/05* (2013.01)

(58) Field of Classification Search
    USPC .................................................. 606/232, 219
    See application file for complete search history.

(56) References Cited

U.S. PATENT DOCUMENTS

| | | |
|---|---|---|
| 3,727,614 A | 4/1973 | Kniazuk |
| 3,773,034 A | 11/1973 | Burns et al. |
| 3,598,576 A | 5/1976 | Komiya |
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,290,151 A | 9/1981 | Massana |
| 4,384,406 A | 5/1983 | Tischlinger |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | MacKin |
| 4,798,594 A | 1/1989 | Hillstead |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | MacKin |
| 5,053,047 A | 10/1991 | Yoon |
| 5,064,431 A | 11/1991 | Gilbertson et al. |
| 5,078,731 A | 1/1992 | Hayhurst |
| 5,084,058 A | 1/1992 | Li |
| 5,103,804 A | 4/1992 | Abele et al. |
| 5,108,368 A | 4/1992 | Hammerslag et al. |
| 5,133,723 A | 7/1992 | Li et al. |
| 5,221,255 A | 6/1993 | Mahurkar et al. |
| 5,221,269 A | 6/1993 | Miller et al. |
| 5,242,456 A | 9/1993 | Nash et al. |
| 5,242,457 A | 9/1993 | Akopov et al. |
| 5,257,975 A | 11/1993 | Foshee |
| 5,312,341 A | 5/1994 | Turi |
| 5,324,298 A | 6/1994 | Phillips et al. |
| 5,346,500 A | 9/1994 | Suchart |
| 5,358,479 A | 10/1994 | Wilson |
| 5,358,514 A | 10/1994 | Schulman et al. |
| 5,364,407 A | 11/1994 | Poll |
| 5,366,479 A | 11/1994 | McGarry et al. |
| 5,368,591 A | 11/1994 | Lennox et al. |
| 5,372,604 A * | 12/1994 | Trott .................. A61B 17/0401 411/922 |
| 5,383,905 A | 1/1995 | Golds et al. |
| 5,409,483 A | 4/1995 | Campbell et al. |
| 5,409,499 A | 4/1995 | Yi |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,760 A | 4/1996 | Wynne et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,531,686 A | 7/1996 | Lundquist et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,590 A | 5/1997 | Wilk |
| 5,626,614 A | 5/1997 | Hart |
| 5,630,824 A | 5/1997 | Hart |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,240 A | 6/1998 | Johnson |
| 5,769,812 A | 6/1998 | Stevens et al. |
| 5,782,861 A | 7/1998 | Cragg et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,860,992 A | 1/1999 | Daniel et al. |
| 5,860,993 A | 1/1999 | Thompson et al. |
| 5,868,733 A | 2/1999 | Ockuly et al. |
| 5,879,371 A | 3/1999 | Gardiner et al. |
| 5,885,238 A | 3/1999 | Stevens et al. |

(56) References Cited

U.S. PATENT DOCUMENTS

| | | |
|---|---|---|
| 5,888,240 A | 3/1999 | Carpentier et al. |
| 5,902,321 A | 5/1999 | Caspari et al. |
| 5,904,651 A | 5/1999 | Swanson et al. |
| 5,906,579 A | 5/1999 | Vander Salm et al. |
| 5,911,717 A | 6/1999 | Jacobsen et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,015,428 A | 1/2000 | Pagedas |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,099,553 A | 8/2000 | Hart et al. |
| 6,102,945 A | 8/2000 | Campbell |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,171,329 B1 | 1/2001 | Shaw et al. |
| 6,183,469 B1 | 2/2001 | Thapliyal et al. |
| 6,197,017 B1 | 3/2001 | Brock et al. |
| 6,221,084 B1 | 4/2001 | Fleenor |
| 6,228,055 B1 | 5/2001 | Foerster et al. |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,432,123 B2 | 8/2002 | Schwartz et al. |
| 6,461,327 B1 | 10/2002 | Addis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,551,332 B1 | 4/2003 | Nguyen et al. |
| 6,575,971 B2 | 6/2003 | Hauck et al. |
| 6,575,987 B2 | 6/2003 | Gellman et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,626,910 B1 * | 9/2003 | Hugues ............... A61B 17/1714 606/151 |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,746,457 B2 | 6/2004 | Dana et al. |
| 6,749,622 B2 | 6/2004 | McGuckin et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,802,851 B2 | 10/2004 | Jones et al. |
| 6,811,560 B2 | 11/2004 | Jones et al. |
| 6,818,001 B2 | 11/2004 | Wulfman et al. |
| 6,875,224 B2 | 4/2005 | Grimes |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,044,957 B2 | 5/2006 | Foerster et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,326,231 B2 | 2/2008 | Phillips et al. |
| 7,344,544 B2 | 3/2008 | Bender et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,655,040 B2 | 2/2010 | Douk et al. |
| 7,666,193 B2 | 2/2010 | Starksen et al. |
| 7,727,247 B2 | 6/2010 | Kimura et al. |
| 7,753,858 B2 | 7/2010 | Starksen et al. |
| 7,753,922 B2 | 7/2010 | Starksen |
| 7,753,924 B2 | 7/2010 | Starksen et al. |
| 7,758,637 B2 | 7/2010 | Starksen et al. |
| 7,766,812 B2 | 8/2010 | Schroeder et al. |
| 7,883,538 B2 | 2/2011 | To et al. |
| 7,918,787 B2 | 4/2011 | Saadat |
| 7,922,762 B2 | 4/2011 | Starksen |
| 7,993,368 B2 | 8/2011 | Gambale et al. |
| 8,066,766 B2 | 11/2011 | To et al. |
| 8,287,555 B2 | 10/2012 | Starksen et al. |
| 8,287,557 B2 | 10/2012 | To et al. |
| 8,343,173 B2 | 1/2013 | Starksen et al. |
| 8,641,727 B2 | 2/2014 | Starksen et al. |
| 9,072,513 B2 | 7/2015 | To et al. |
| 9,226,825 B2 | 1/2016 | Starksen et al. |
| 9,468,528 B2 | 10/2016 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0034528 A1 | 10/2001 | Foerster et al. |
| 2001/0041821 A1 | 11/2001 | Wilk |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |

(56) References Cited

U.S. PATENT DOCUMENTS

| | | |
|---|---|---|
| 2002/0087169 A1 | 7/2002 | Brock et al. |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |
| 2002/0193815 A1 | 12/2002 | Foerster et al. |
| 2003/0009196 A1 | 1/2003 | Peterson |
| 2003/0014060 A1 | 1/2003 | Wilson |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078601 A1 | 4/2003 | Shikhman et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0093024 A1 | 5/2004 | Lousararian et al. |
| 2004/0097788 A1 | 5/2004 | Mourlas et al. |
| 2004/0122450 A1 | 6/2004 | Oren et al. |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0021054 A1 | 1/2005 | Ainsworth et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0065589 A1 | 3/2005 | Schneider et al. |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1* | 5/2005 | Starksen et al. .............. 606/143 |
| 2005/0107812 A1 | 5/2005 | Starksen et al. |
| 2005/0107871 A1 | 5/2005 | Realyvasquez et al. |
| 2005/0119523 A1 | 6/2005 | Starksen et al. |
| 2005/0119673 A1 | 6/2005 | Gordon et al. |
| 2005/0137689 A1 | 6/2005 | Salahieh et al. |
| 2005/0184122 A1 | 8/2005 | Hlavka et al. |
| 2005/0192599 A1 | 9/2005 | Demarais |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0267495 A1 | 12/2005 | Ginn et al. |
| 2005/0273138 A1* | 12/2005 | To et al. .............. 606/219 |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0015144 A1 | 1/2006 | Burbank et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0282161 A1 | 12/2006 | Huynh et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0172035 A1 | 7/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0049213 A1 | 2/2010 | Serina et al. |
| 2010/0076548 A1 | 3/2010 | Konno |
| 2010/0082098 A1 | 4/2010 | Starksen et al. |
| 2010/0094314 A1 | 4/2010 | Hernlund et al. |
| 2010/0121349 A1 | 5/2010 | Meier et al. |
| 2011/0160528 A1 | 6/2011 | Starksen |
| 2012/0101442 A1 | 4/2012 | Legaspi et al. |
| 2012/0271331 A1 | 10/2012 | To et al. |
| 2013/0304093 A1 | 11/2013 | Serina et al. |
| 2014/0135799 A1 | 5/2014 | Henderson |
| 2014/0155783 A1 | 6/2014 | Starksen et al. |
| 2014/0188140 A1 | 7/2014 | Meier et al. |
| 2014/0194976 A1 | 7/2014 | Starksen et al. |
| 2014/0303649 A1 | 10/2014 | Nguyen et al. |

(56) References Cited

U.S. PATENT DOCUMENTS

| | | |
|---|---|---|
| 2015/0164639 A1 | 6/2015 | Starksen et al. |
| 2015/0182216 A1 | 7/2015 | Morales et al. |
| 2017/0224489 A1 | 8/2017 | Starksen et al. |

FOREIGN PATENT DOCUMENTS

| | | |
|---|---|---|
| GB | 1370546 A | 10/1974 |
| JP | 6-510460 A | 11/1994 |
| JP | 11-506628 A | 6/1999 |
| JP | 2004-601 A | 1/2004 |
| JP | 2004-530451 A | 10/2004 |
| JP | 2007-514455 A | 6/2007 |
| JP | 48-23295 B2 | 11/2011 |
| WO | WO-93/08740 A1 | 5/1993 |
| WO | WO-94/03227 A1 | 2/1994 |
| WO | WO-95/15715 A1 | 6/1995 |
| WO | WO-96/08208 A1 | 3/1996 |
| WO | WO-96/39081 A1 | 12/1996 |
| WO | WO-96/39942 A1 | 12/1996 |
| WO | WO-97/27799 A1 | 8/1997 |
| WO | WO-97/27807 A1 | 8/1997 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-2002/034167 A3 | 1/2002 |
| WO | WO-02/34167 A2 | 5/2002 |
| WO | WO-02/34167 A3 | 5/2002 |
| WO | WO-2002/034167 A2 | 5/2002 |
| WO | WO-02/051329 A1 | 7/2002 |
| WO | WO-02/053011 A2 | 7/2002 |
| WO | WO-02/053011 A3 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/001936 A2 | 1/2007 |
| WO | WO-2007/001936 A3 | 1/2007 |
| WO | WO-2007/005495 A1 | 1/2007 |
| WO | WO-2007/021564 A1 | 2/2007 |
| WO | WO-2007/021597 A2 | 2/2007 |
| WO | WO-2007/021597 A3 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2008/028135 A2 | 3/2008 |
| WO | WO-2008/028135 A3 | 3/2008 |

OTHER PUBLICATIONS

Written Opinion of the International Searching Authority dated Feb. 21, 2012, for PCT Patent Application No. PCT/US2011/050331, filed on Sep. 2, 2011, 4 pages.

De Simone, R. et al. (Apr. 15, 1993). "Adjustable Tricuspid Valve Annuloplasty Assisted by Intraoperative Transesophageal Color Doppler Echocardiography," Am. J. Cardiol. 71(11):926-931.

De Simone, R. et al. (Apr. 1, 1994). "Adjustable Annuloplasty for Tricuspid Insufficiency with External Control," Reader's Comments and Reply, Am. J. Cardiol. 73(9):721-722.

Downing, S.W. et al. (2002). "Feasibility of Off-Pump ASD Closure Using Real-Time 3-D Echocardiography," The Heart Surgery Forum 5(2):96-99, Abstract 7025.

European Examination Communication dated Dec. 8, 2009, for EP Application No. 06 837 222.6 filed on Nov. 8, 2006, three pages.

Extended European Search Report dated Sep. 9, 2011, for EP Patent Application No. 11158896.8, filed on Sep. 1, 2004, 7 pages.

Extended European Search Report dated Sep. 16, 2011, for EP Patent Application No. 11158898.4, filed on Sep. 1, 2004, 8 pages.

Final Office Action dated Feb. 6, 2007, for U.S. Appl. No. 10/656,797, filed Sep. 4, 2003, 8 pages.

Final Office Action dated Jul. 12, 2007, for U.S. Appl. No. 11/202,474, filed Aug. 11, 2005, 10 pages.

Final Office Action dated Jul. 24, 2007, for U.S. Appl. No. 10/741,130, filed Dec. 19, 2003, 10 pages.

Final Office Action dated Aug. 6, 2007, for U.S. Appl. No. 10/901,019, filed Jul. 27, 2004, 12 pages.

Final Office Action dated Aug. 6, 2007, for U.S. Appl. No. 11/137,833, filed May 24, 2005, 8 pages.

Final Office Action dated Aug. 13, 2007, for U.S. Appl. No. 10/900,980, filed Jul. 27, 2004, 9 pages.

Final Office Action dated Aug. 14, 2007, for U.S. Appl. No. 11/255,400, filed Oct. 20, 2005, 8 pages.

Final Office Action dated Aug. 30, 2007, for U.S. Appl. No. 11/232,190, filed Sep. 20, 2005, 9 pages.

Final Office Action dated Oct. 30, 2007, for U.S. Appl. No. 10/656,797, filed Sep. 4, 2003, 6 pages.

Final Office Action dated Apr. 2, 2008, for U.S. Appl. No. 10/792,681, filed Mar. 2, 2004, 15 pages.

Final Office Action dated Apr. 14, 2008, for U.S. Appl. No. 10/901,019, filed Jul. 27, 2004, 11 pages.

Final Office Action dated May 28, 2008, for U.S. Appl. No. 11/270,034, filed Nov. 8, 2005, 10 pages.

Final Office Action dated Jun. 4, 2008, for U.S. Appl. No. 11/202,474, filed Aug. 11, 2005, 10 pages.

Final Office Action dated Aug. 1, 2008, for U.S. Appl. No. 11/232,190, filed Sep. 20, 2005, 8 pages.

Final Office Action dated Sep. 30, 2008, for U.S. Appl. No. 10/900,980, filed Jul. 27, 2004, 7 pages.

Final Office Action dated Oct. 14, 2008, for U.S. Appl. No. 10/741,130, filed Dec. 19, 2003, 9 pages.

Final Office Action dated Jan. 22, 2009, for U.S. Appl. No. 11/255,400, filed Oct. 20, 2005, 9 pages.

Final Office Action dated Mar. 11, 2009, for U.S. Appl. No. 10/656,797, filed Sep. 4, 2003, 10 pages.

Final Office Action dated Apr. 10, 2009, for U.S. Appl. No. 11/414,657, filed Apr. 27, 2006, 8 pages.

Final Office Action dated Apr. 10, 2009, for U.S. Appl. No. 11/255,400, filed Oct. 20, 2005, 8 pages.

Final Office Action dated Apr. 29, 2009, for U.S. Appl. No. 10/901,019, filed Jul. 27, 2004, 9 pages.

Final Office Action dated Jul. 21, 2009, for U.S. Appl. No. 11/270,034, filed Nov. 8, 2005, 8 pages.

Final Office Action dated Sep. 2, 2009, for U.S. Appl. No. 11/232,190, filed Sep. 20, 2005, 8 pages.

Final Office Action dated Sep. 28, 2009, for U.S. Appl. No. 11/202,474, filed Aug. 11, 2005, 10 pages.

Final Office Action dated Oct. 13, 2009, for U.S. Appl. No. 10/901,554, filed Jul. 27, 2004, 11 pages.

Final Office Action dated Nov. 10, 2009, for U.S. Appl. No. 10/741,130, filed Dec. 19, 2003, 9 pages.

(56) References Cited

OTHER PUBLICATIONS

Final Office Action dated Mar. 3, 2010, for U.S. Appl. No. 11/414,657, filed Apr. 27, 2006, 7 pages.
Final Office Action dated Mar. 25, 2010, for U.S. Appl. No. 10/900,980, filed Jul. 27, 2004, 8 pages.
Final Office Action dated Jun. 8, 2010, for U.S. Appl. No. 10/792,681, filed Mar. 2, 2004, 17 pages.
Final Office Action dated Jul. 26, 2010, for U.S. Appl. No. 11/270,034, filed Nov. 8, 2005, 8 pages.
Final Office Action dated Sep. 15, 2010, for U.S. Appl. No. 11/894,401, filed Aug. 20, 2007, 6 pages.
Final Office Action dated Oct. 6, 2010, for U.S. Appl. No. 12/132,375, filed Jun. 3, 2008, 9 pages.
Final Office Action dated Nov. 26, 2010, for U.S. Appl. No. 11/894,340, filed Aug. 20, 2007, 12 pages.
Final Office Action dated Nov. 29, 2010, for U.S. Appl. No. 11/894,463, filed Aug. 20, 2007, 12 pages.
Final Office Action dated Feb. 24, 2011, for U.S. Appl. No. 11/894,397, filed Aug. 20, 2007, 12 pages.
Final Office Action dated Feb. 24, 2011, for U.S. Appl. No. 11/894,468, filed Aug. 20, 2007, 12 pages.
Final Office Action dated Mar. 17, 2011, for U.S. Appl. No. 10/901,554, filed Jul. 27, 2004, 13 pages.
Final Office Action dated Mar. 17, 2011, for U.S. Appl. No. 11/202,474, filed Aug. 11, 2005, 9 pages.
Final Office Action dated Apr. 20, 2011, for U.S. Appl. No. 11/414,657, filed Apr. 27, 2006, 8 pages.
Final Office Action dated Aug. 4, 2011, for U.S. Appl. No. 10/900,980, filed Jul. 27, 2004, 9 pages.
Final Office Action dated Nov. 3, 2011, for U.S. Appl. No. 12/581,040, filed Oct. 16, 2009, 5 pages.
Final Office Action dated Nov. 10, 2011, for U.S. Appl. No. 10/792,681, filed Mar. 2, 2004, 20 pages.
Final Office Action dated Dec. 6, 2011, for U.S. Appl. No. 12/366,553, filed Feb. 5, 2009, 7 pages.
Final Office Action dated Mar. 19, 2012, for U.S. Appl. No. 12/574,563, filed Oct. 6, 2009, 6 pages.
Final Office Action dated Jun. 11, 2012, for U.S. Appl. No. 12/132,161, filed Jun. 3, 2008, 13 pages.
Final Office Action dated Jun. 11, 2012, for U.S. Appl. No. 12/187,331, filed Jun. 6, 2008, 7 pages.
Final Office Action dated Feb. 2, 2015, for U.S. Appl. No. 13/540,499, filed Jul. 2, 2012, 10 pages.
International Search Report dated Dec. 19, 2006, for PCT Application No. PCT/US2006/031190, filed Aug. 10, 2006, four pages.
International Search Report dated Apr. 2, 2007, for PCT Application No. PCT/US2006/043597, filed Nov. 8, 2006, seven pages.
Nagy, Z.L. et al. (Dec. 2000). "Mitral Annuloplasty with a Suture Technique," European Journal of Cardio-thoracic Surgery 18(6):739-740.
Non-Final Office Action dated Aug. 9, 2006, for U.S. Appl. No. 10/900,980, filed Jul. 27, 2004, 17 pages.
Non-Final Office Action dated Aug. 22, 2006, for U.S. Appl. No. 10/656,797, filed Sep. 4, 2003, 6 pages.
Non-Final Office Action dated Nov. 15, 2006, for U.S. Appl. No. 11/137,833, filed May 24, 2005, 12 pages.
Non-Final Office Action dated Nov. 28, 2006, for U.S. Appl. No. 10/901,019, filed Jul. 27, 2004, 20 pages.
Non-Final Office Action dated Dec. 27, 2006, for U.S. Appl. No. 10/741,130, filed Dec. 19, 2003, 9 pages.
Non-Final Office Action dated Dec. 27, 2006, for U.S. Appl. No. 11/270,034, filed Nov. 8, 2005, 8 pages.
Non-Final Office Action dated Jan. 4, 2007, for U.S. Appl. No. 11/255,400, filed Oct. 20, 2005, 7 pages.
Non-Final Office Action dated Feb. 27, 2007, for U.S. Appl. No. 11/202,474, filed Aug. 11, 2005, 8 pages.
Non-Final Office Action dated Mar. 12, 2007, for U.S. Appl. No. 11/232,190, filed Sep. 20, 2005, 11 pages.
Non-Final Office Action dated Jul. 24, 2007, for U.S. Appl. No. 10/656,797, filed Sep. 4, 2003, 6 pages.
Non-Final Office Action dated Aug. 1, 2007, for U.S. Appl. No. 10/792,681, filed Mar. 2, 2004, 16 pages.
Non-Final Office Action dated Aug. 30, 2007, for U.S. Appl. No. 11/270,034, filed Nov. 8, 2005, 10 pages.
Non-Final Office Action dated Oct. 19, 2007, for U.S. Appl. No. 11/202,474, filed Aug. 11, 2005, 7 pages.
Non-Final Office Action dated Oct. 29, 2007, for U.S. Appl. No. 10/901,019, filed Jul. 27, 2004, 10 pages.
Non-Final Office Action dated Nov. 14, 2007, for U.S. Appl. No. 10/741,130, filed Dec. 19, 2003, 8 pages.
Non-Final Office Action dated Nov. 14, 2007, for U.S. Appl. No. 11/137,833, filed May 24, 2005, 8 pages.
Non-Final Office Action dated Jan. 9, 2008, for U.S. Appl. No. 11/232,190, filed Sep. 20, 2005, 8 pages.
Non-Final Office Action dated Jan. 31, 2008, for U.S. Appl. No. 11/255,400, filed Oct. 20, 2005, 7 pages.
Non-Final Office Action (Supplementary) dated May 9, 2008, for U.S. Appl. No. 11/255,400, filed Oct. 20, 2005, 7 pages.
Non-Final Office Action dated Mar. 27, 2008, for U.S. Appl. No. 10/900,980, filed Jul. 27, 2004, 7 pages.
Non-Final Office Action dated Jun. 6, 2008, for U.S. Appl. No. 10/656,797, filed Sep. 4, 2003, 5 pages.
Non-Final Office Action dated Aug. 29, 2008, for U.S. Appl. No. 10/792,681, filed Mar. 2, 2004, 15 pages.
Non-Final Office Action dated Sep. 26, 2008, for U.S. Appl. No. 11/414,657, filed Apr. 27, 2006, 11 pages.
Non-Final Office Action dated Oct. 24, 2008, for U.S. Appl. No. 10/901,019, filed Jul. 27, 2004, 11 pages.
Non-Final Office Action dated Jan. 13, 2009, for U.S. Appl. No. 10/901,555, filed Jul. 27, 2004, 11 pages.
Non-Final Office Action dated Jan. 23, 2009, for U.S. Appl. No. 11/232,190, filed Sep. 20, 2005, 8 pages.
Non-Final Office Action dated Jan. 23, 2009, for U.S. Appl. No. 11/270,034, filed Nov. 8, 2005, 8 pages.
Non-Final Office Action dated Jan. 29, 2009, for U.S. Appl. No. 10/900,980, filed Jul. 27, 2004, 6 pages.
Non-Final Office Action dated Mar. 5, 2009, for U.S. Appl. No. 11/202,474, filed Aug. 11, 2005, 10 pages.
Non-Final Office Action dated Mar. 18, 2009, for U.S. Appl. No. 10/901,554, filed Jul. 27, 2004, 12 pages.
Non-Final Office Action dated Mar. 27, 2009, for U.S. Appl. No. 10/741,130, filed Dec. 19, 2003, 9 pages.
Non-Final Office Action dated Mar. 31, 2009, for U.S. Appl. No. 10/792,681, filed Mar. 2, 2004, 15 pages.
Non-Final Office Action dated Aug. 25, 2009, for U.S. Appl. No. 10/900,980, filed Jul. 27, 2004, 7 pages.
Non-Final Office Action dated Aug. 26, 2009, for U.S. Appl. No. 11/414,657, filed Apr. 27, 2006, 6 pages.
Non-Final Office Action dated Sep. 17, 2009, for U.S. Appl. No. 10/656,797, filed Sep. 4, 2003, 13 pages.
Non-Final Office Action dated Oct. 19, 2009, for U.S. Appl. No. 10/901,019, filed Jul. 27, 2004, 21 pages.
Non-Final Office Action dated Jan. 19, 2010, for U.S. Appl. No. 11/270,034, filed Nov. 8, 2005, 10 pages.
Non-Final Office Action dated Feb. 18, 2010, for U.S. Appl. No. 11/894,401, filed Aug. 20, 2007, 6 pages.
Non-Final Office Action dated Mar. 16, 2010, for U.S. Appl. No. 11/894,340, filed Aug. 20, 2007, 14 pages.
Non-Final Office Action dated Mar. 29, 2010, for U.S. Appl. No. 11/894,463, filed Aug. 20, 2007, 14 pages.
Non-Final Office Action dated Apr. 2, 2010, for U.S. Appl. No. 12/132,375, filed Jun. 3, 2008, 9 pages.
Non-Final Office Action dated Jun. 9, 2010, for U.S. Appl. No. 11/894,468, filed Aug. 20, 2007, 14 pages.
Non-Final Office Action dated Jun. 21, 2010, for U.S. Appl. No. 11/894,397, filed Aug. 20, 2007, 13 pages.
Non-Final Office Action dated Aug. 17, 2010, for U.S. Appl. No. 11/414,657, filed Apr. 27, 2006, 7 pages.
Non-Final Office Action dated Aug. 20, 2010, for U.S. Appl. No. 10/901,554, filed Jul. 27, 2004, 13 pages.
Non-Final Office Action dated Oct. 8, 2010, for U.S. Appl. No. 11/894,368, filed Aug. 20, 2007, 10 pages.

(56) References Cited

OTHER PUBLICATIONS

Non-Final Office Action dated Oct. 25, 2010, for U.S. Appl. No. 11/202,474, filed Aug. 11, 2005, 8 pages.
Non-Final Office Action dated Oct. 29, 2010, for U.S. Appl. No. 11/894,530, filed Aug. 20, 2007, 11 pages.
Non-Final Office Action dated Nov. 24, 2010, for U.S. Appl. No. 10/900,980, filed Jul. 27, 2004, 8 pages.
Non-Final Office Action dated Feb. 2, 2011, for U.S. Appl. No. 12/581,040, filed Oct. 16, 2009, 5 pages.
Non-Final Office Action dated Apr. 27, 2011, for U.S. Appl. No. 12/366,533, filed Feb. 5, 2009, 9 pages.
Non-Final Office Action dated Jul. 29, 2011, for U.S. Appl. No. 12/574,563, filed Oct. 6, 2009, 5 pages.
Non-Final Office Action dated Oct. 13, 2011, for U.S. Appl. No. 12/187,331, filed Aug. 6, 2008, 5 pages.
Non-Final Office Action dated Oct. 18, 2011, for U.S. Appl. No. 12/132,161, filed Jun. 3, 2008, 15 pages.
Non-Final Office Action dated Oct. 18, 2011, for U.S. Appl. No. 10/741,130, filed Dec. 19, 2003, 9 pages.
Non-Final Office Action dated Dec. 22, 2011, for U.S. Appl. No. 11/270,034, filed Nov. 8, 2005, 9 pages.
Non-Final Office Action dated Jun. 7, 2012, for U.S. Appl. No. 12/850,531, filed Aug. 4, 2010, 8 pages.
Non-Final Office Action dated Apr. 8, 2013, for U.S. Appl. No. 11/414,657, filed Apr. 27, 2006, 9 pages.
Non-Final Office Action dated Nov. 7, 2014, for U.S. Appl. No. 12/187,331, filed Aug. 6, 2008, 8 pages.
Notice of Allowance dated Aug. 4, 2009, for U.S. Appl. No. 10/901,555, filed Jul. 27, 2004, 7 pages.
Notice of Allowance dated Feb. 24, 2010, for U.S. Appl. No. 10/656,797, filed Sep. 4, 2003, 10 pages.
Notice of Allowance dated Apr. 28, 2010, for U.S. Appl. No. 10/901,019, filed Jul. 27, 2004, 7 pages.
Notice of Allowance dated Nov. 17, 2010, for U.S. Appl. No. 11/232,190, filed Sep. 20, 2005, 11 pages.
Notice of Allowance dated Dec. 6, 2010, for U.S. Appl. No. 12/132,375, filed Jun. 3, 2008, 9 pages.
Notice of Allowance dated Jul. 26, 2011, for U.S. Appl. No. 11/894,530, filed Aug. 20, 2007, 10 pages.
Notice of Allowance dated Jun. 11, 2012, for U.S. Appl. No. 10/741,130, filed Dec. 19, 2003, 9 pages.
Notice of Allowance dated Sep. 25, 2013, for U.S. Appl. No. 12/132,161, filed Jun. 3, 2008, 12 pages.
Shumway, S.J. et al. (Dec. 1988). "A 'Designer' Annuloplasty Ring for Patients with Massive Mitral Annular Dilatation," *Ann. Thorac. Surg.* 46(6):695-696.

Supplementary European Search Report dated Nov. 10, 2008, for EP Application No. 04 78 2847, filed on Sep. 1, 2004, 2 pages.
Final Office Action dated Apr. 27, 2009, for U.S. Appl. No. 10/901,455, filed Jul. 27, 2004, 11 pages.
Final Office Action dated Feb. 4, 2016, for U.S. Appl. No. 14/626,826, filed Feb. 19, 2015, 9 pages.
International Search Report dated Mar. 7, 2007, for PCT Patent Application No. PCT/US2004/028431, filed on Sep. 1, 2004, 1 page.
Non-Final Office Action dated Apr. 29, 2008, for U.S. Appl. No. 10/901,455, filed Jul. 27, 2004, 9 pages.
Non-Final Office Action dated Oct. 8, 2009, for U.S. Appl. No. 10/901,455, filed Jul. 27, 2004, 10 pages.
Non-Final Office Action dated Oct. 20, 2011, for U.S. Appl. No. 12/824,051, filed Jun. 25, 2010, 8 pages.
Non-Final Office Action dated Nov. 24, 2015, for U.S. Appl. No. 14/156,347, filed Jan. 15, 2014, 5 pages.
Non-Final Office Action dated Apr. 21, 2016, for U.S. Appl. No. 13/540,499, filed Jul. 2, 2012, 12 pages.
Notice of Allowance dated May 5, 2010, for U.S. Appl. No. 10/901,455, filed Jul. 27, 2004, 8 pages.
Notice of Allowance dated Jun. 15, 2016, for U.S. Appl. No. 14/156,347, filed Jan. 15, 2014, 7 pages.
Notice of Allowance dated Oct. 29, 2015, for U.S. Appl. No. 10/901,554, filed Jul. 27, 2004, 8 pages.
Notice of Allowance dated Aug. 6, 2009, for U.S. Appl. No. 11/255,400, filed Oct. 20, 2005, 2 pages.
Notice of Allowance dated Jun. 8, 2012, for U.S. Appl. No. 11/894,401, filed Aug. 20, 2007, 9 pages.
Notice of Allowance dated Mar. 2, 2015, for U.S. Appl. No. 12/187,331, filed Aug. 6, 2008, 5 pages.
Written Opinion of the International Searching Authority dated Mar. 7, 2007, for PCT Patent Application No. PCT/US2004/028431, filed on Sep. 1, 2004, 4 pages.
Written Opinion of the International Searching Authority dated Dec. 19, 2006, for PCT Application No. PCT/US2006/031190, filed Aug. 10, 2006, 6 pages.
Written Opinion of the International Searching Authority dated Apr. 2, 2007, for PCT Application No. PCT/US2006/043597, filed Nov. 8, 2006, 7 pages.
U.S. Appl. No. 15/265,781, filed Sep. 14, 2016, by Starksen et al.
Non-Final Office Action dated Jan. 26, 2017, for U.S. Appl. No. 13/540,499, filed Jul. 2, 2012, 10 pages.
Non-Final Office Action dated Feb. 17, 2017, for U.S. Appl. No. 14/626,826, filed Feb. 19, 2015, 11 pages.
Final Office Action dated on Nov. 3, 2017, for U.S. Appl. No. 13/540,499, filed on Jul. 2, 2012, 10 pages.

* cited by examiner

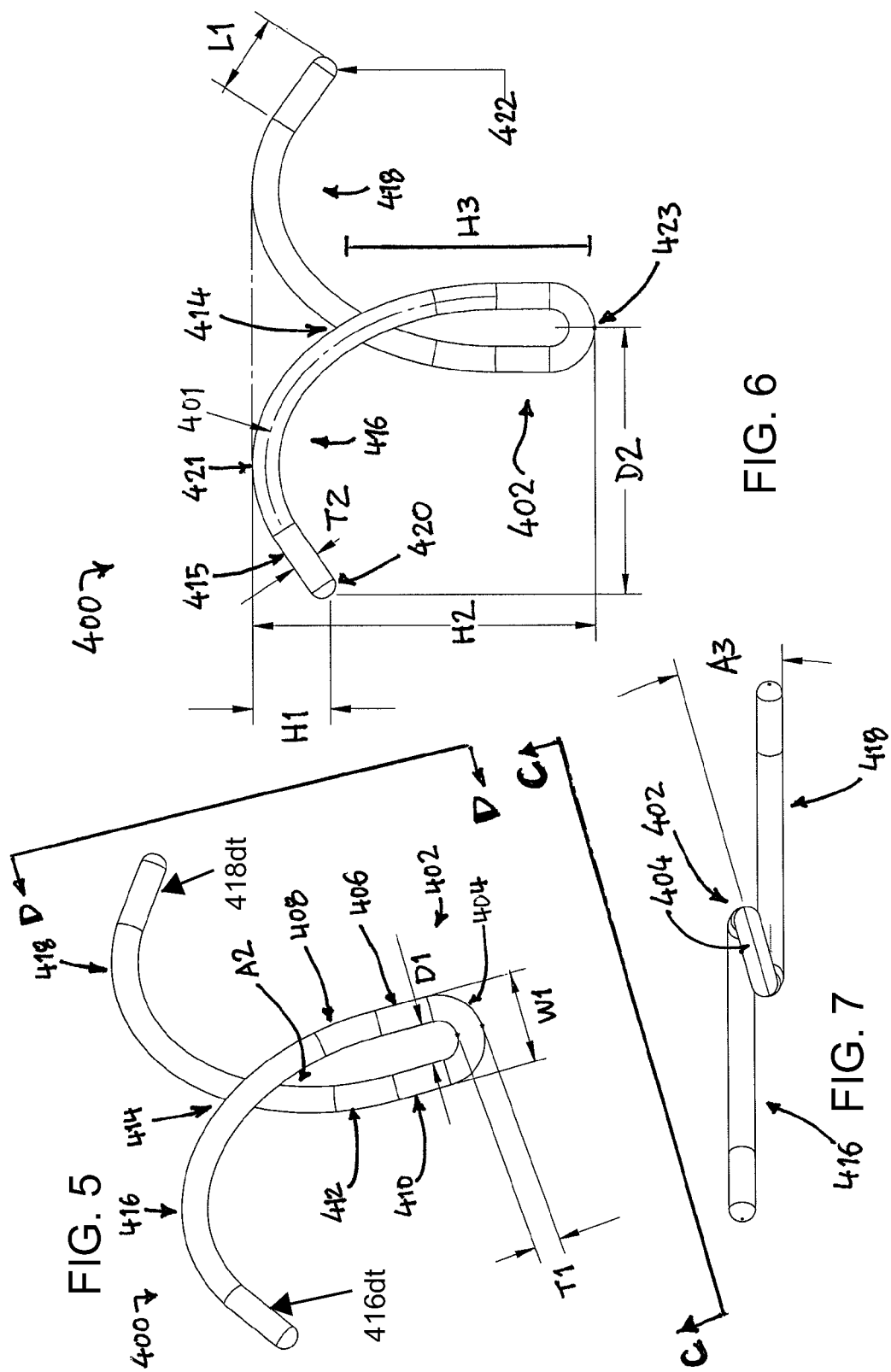

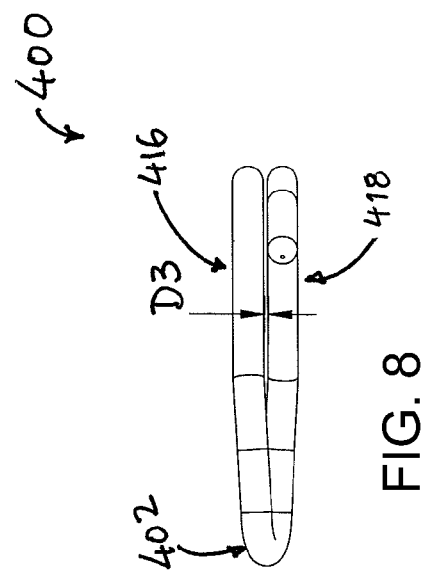

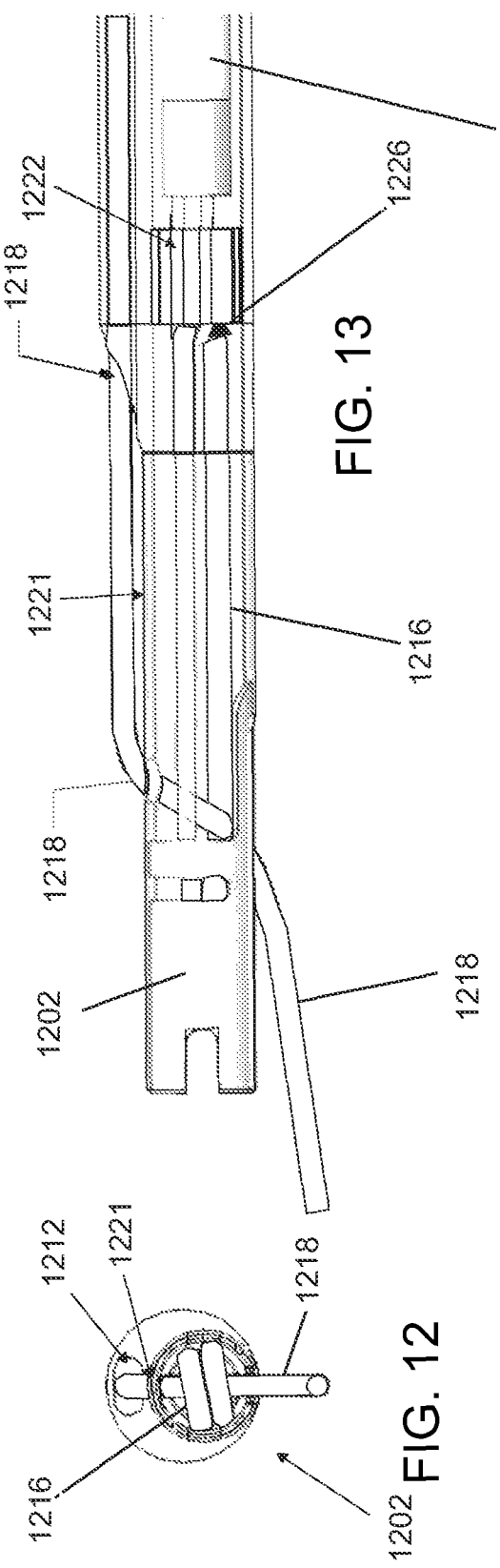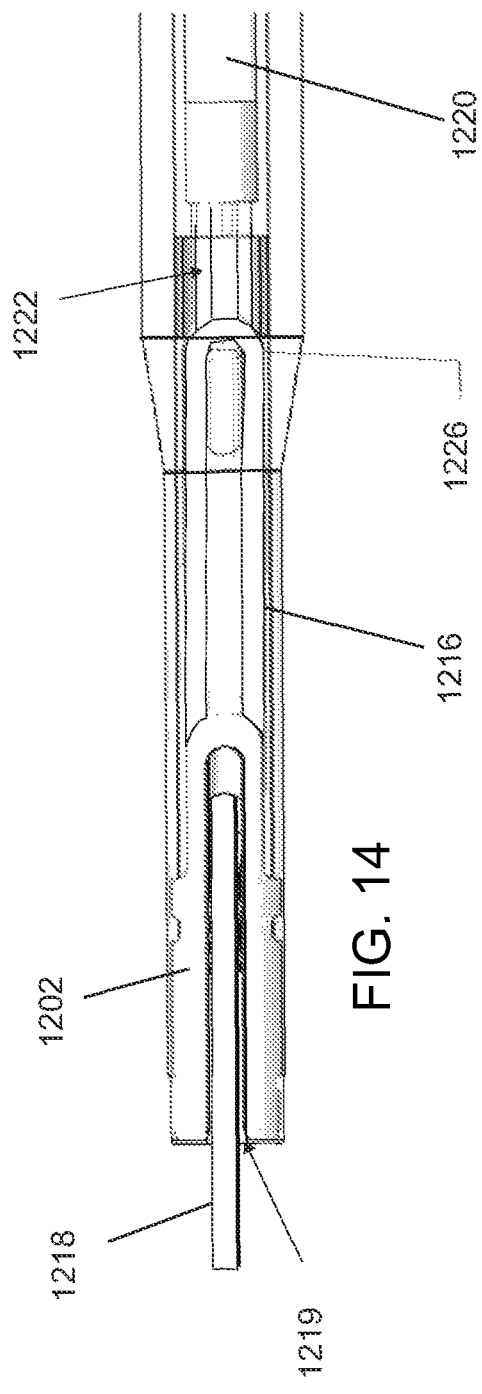
FIG. 12
FIG. 13
FIG. 14

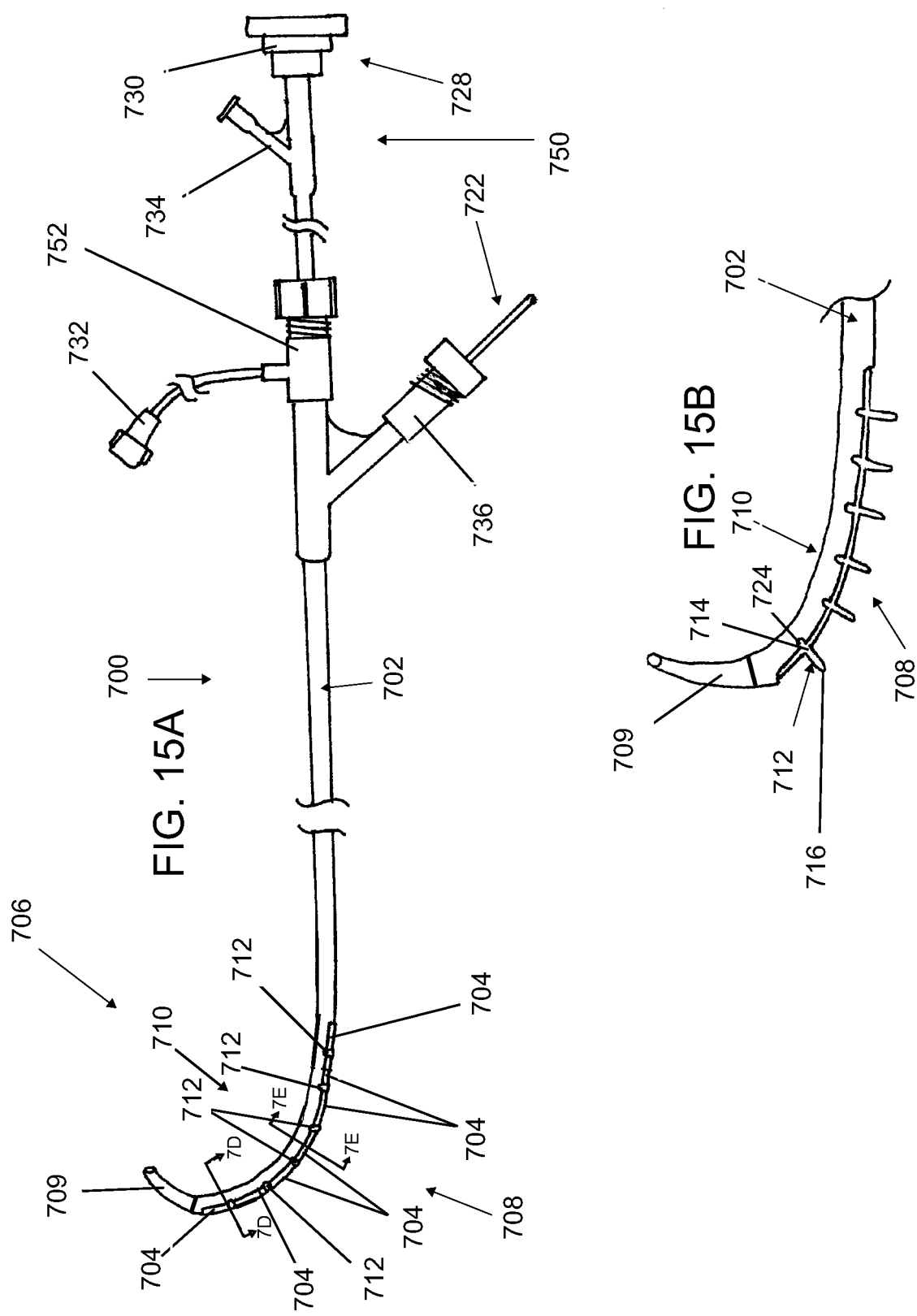

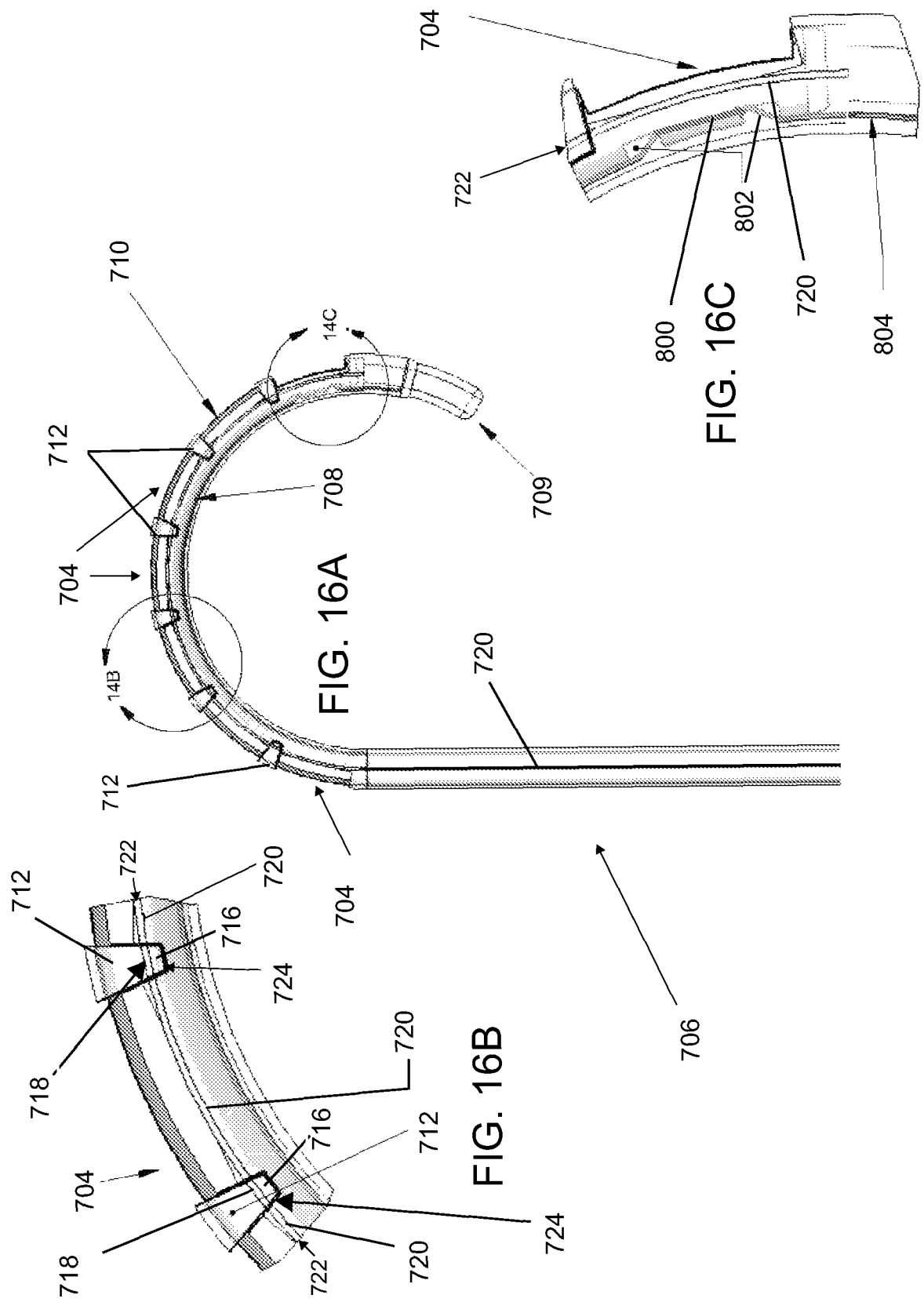

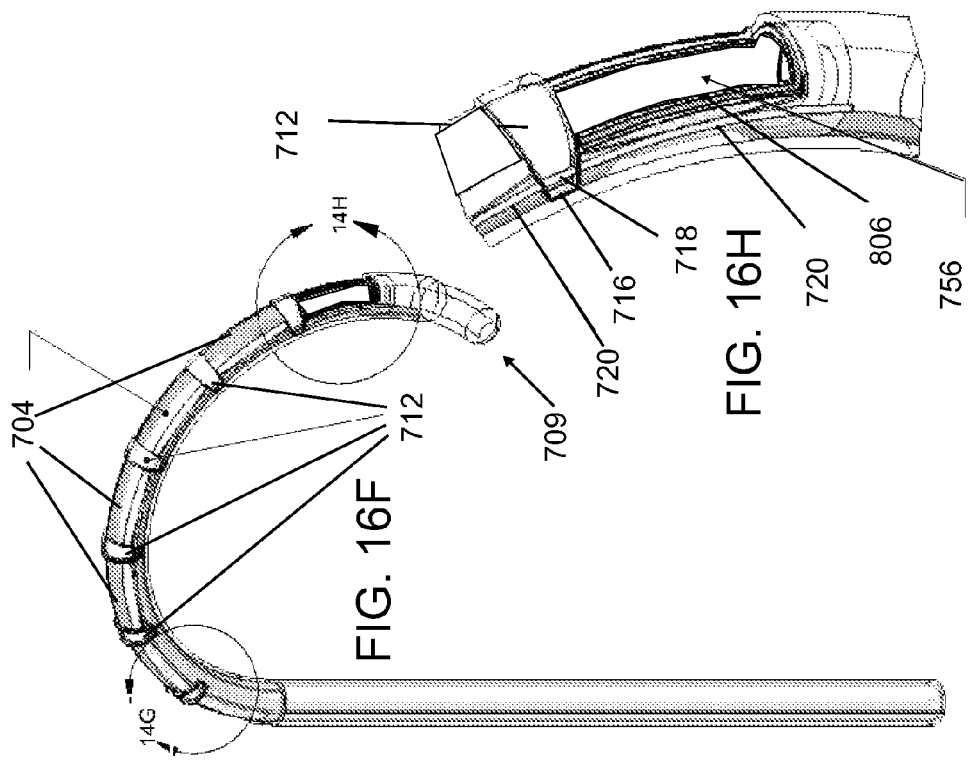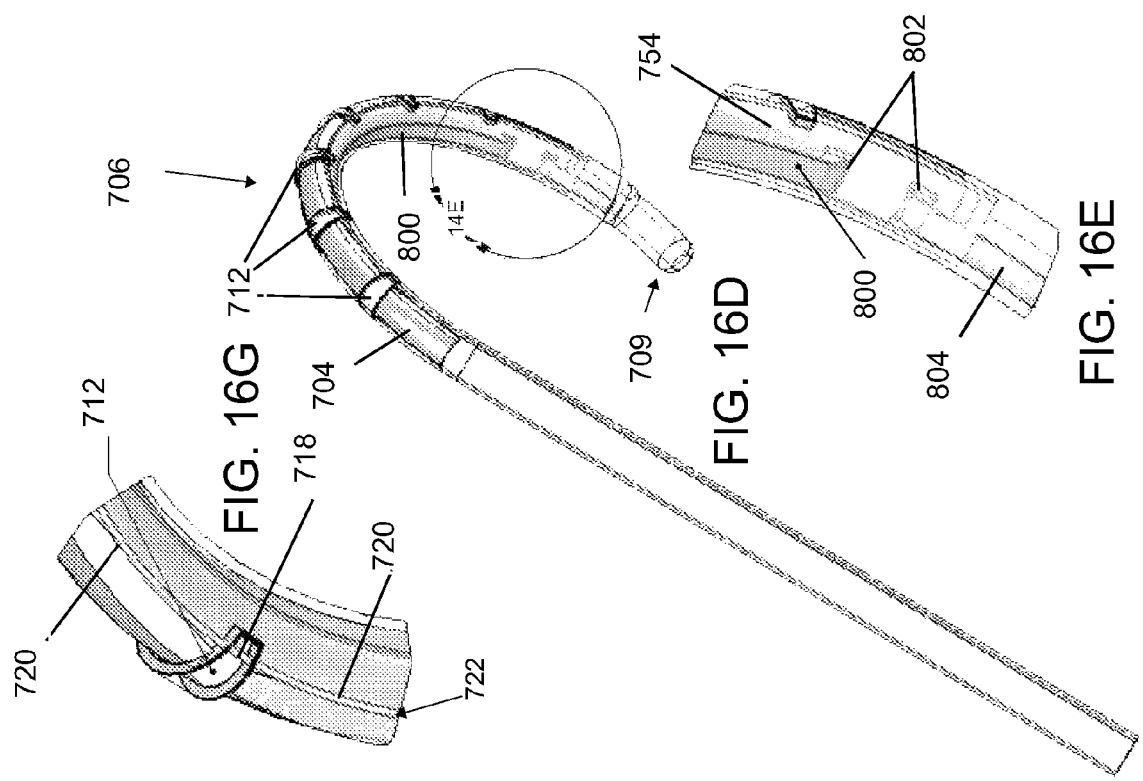

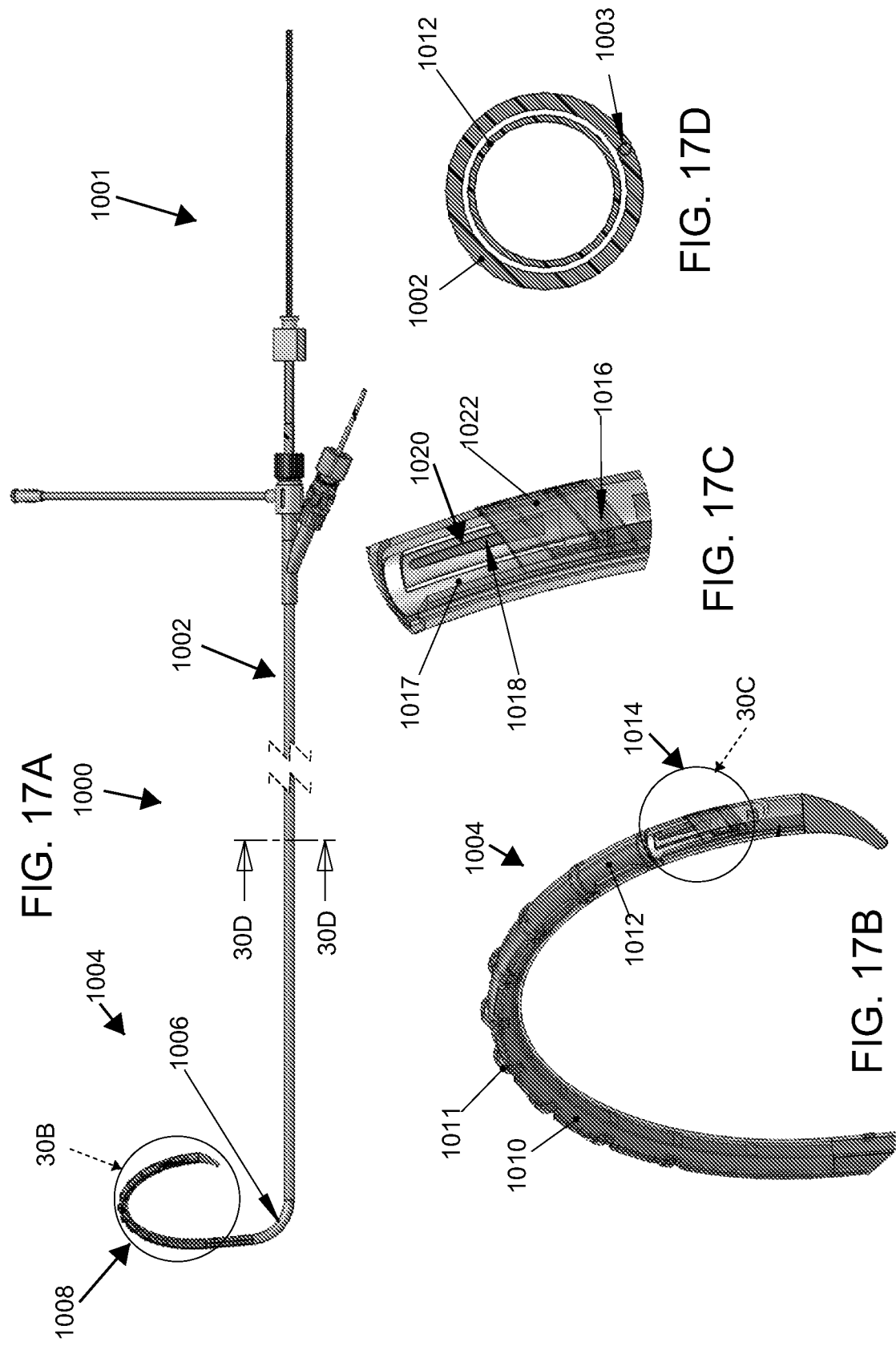

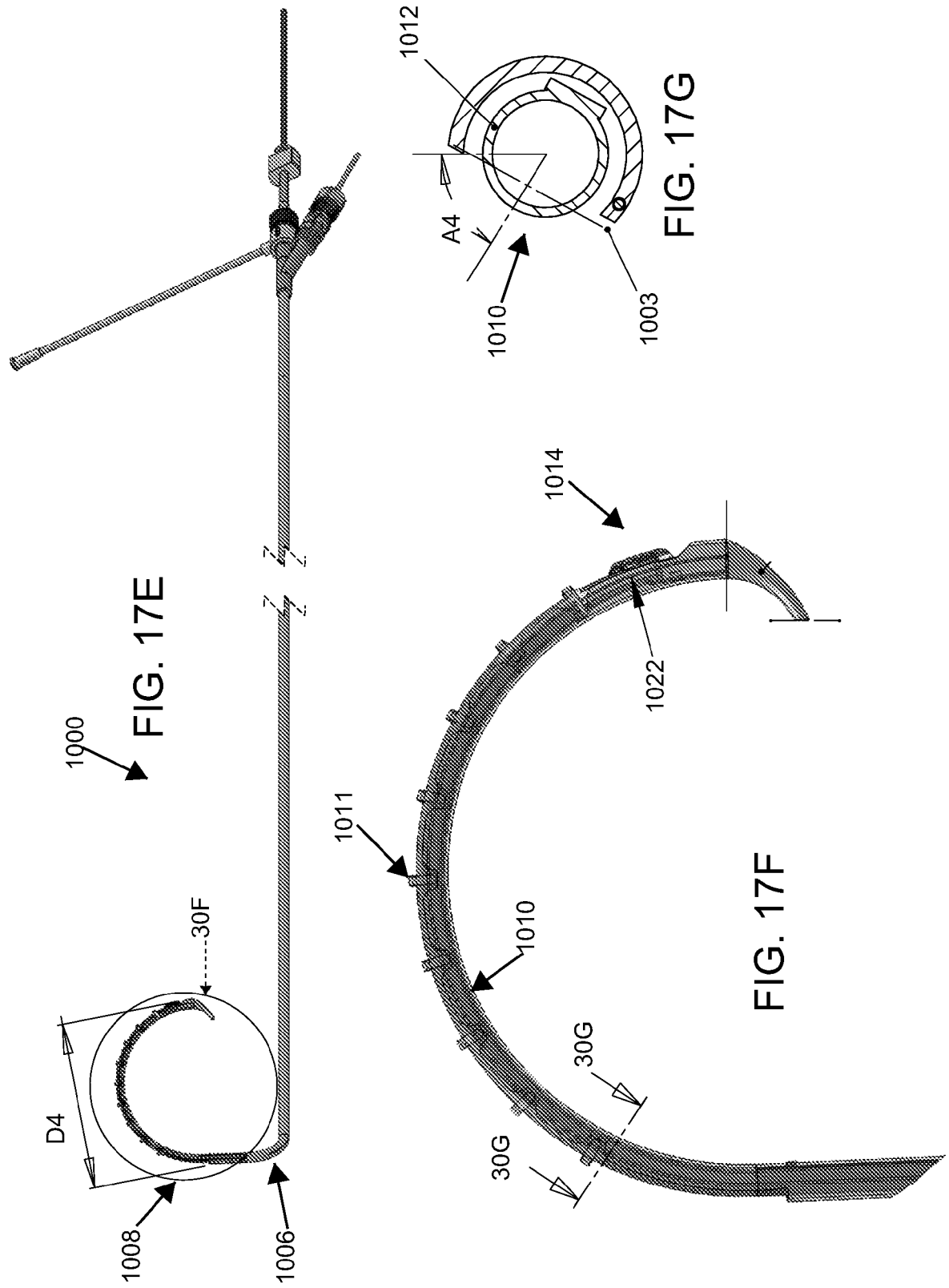

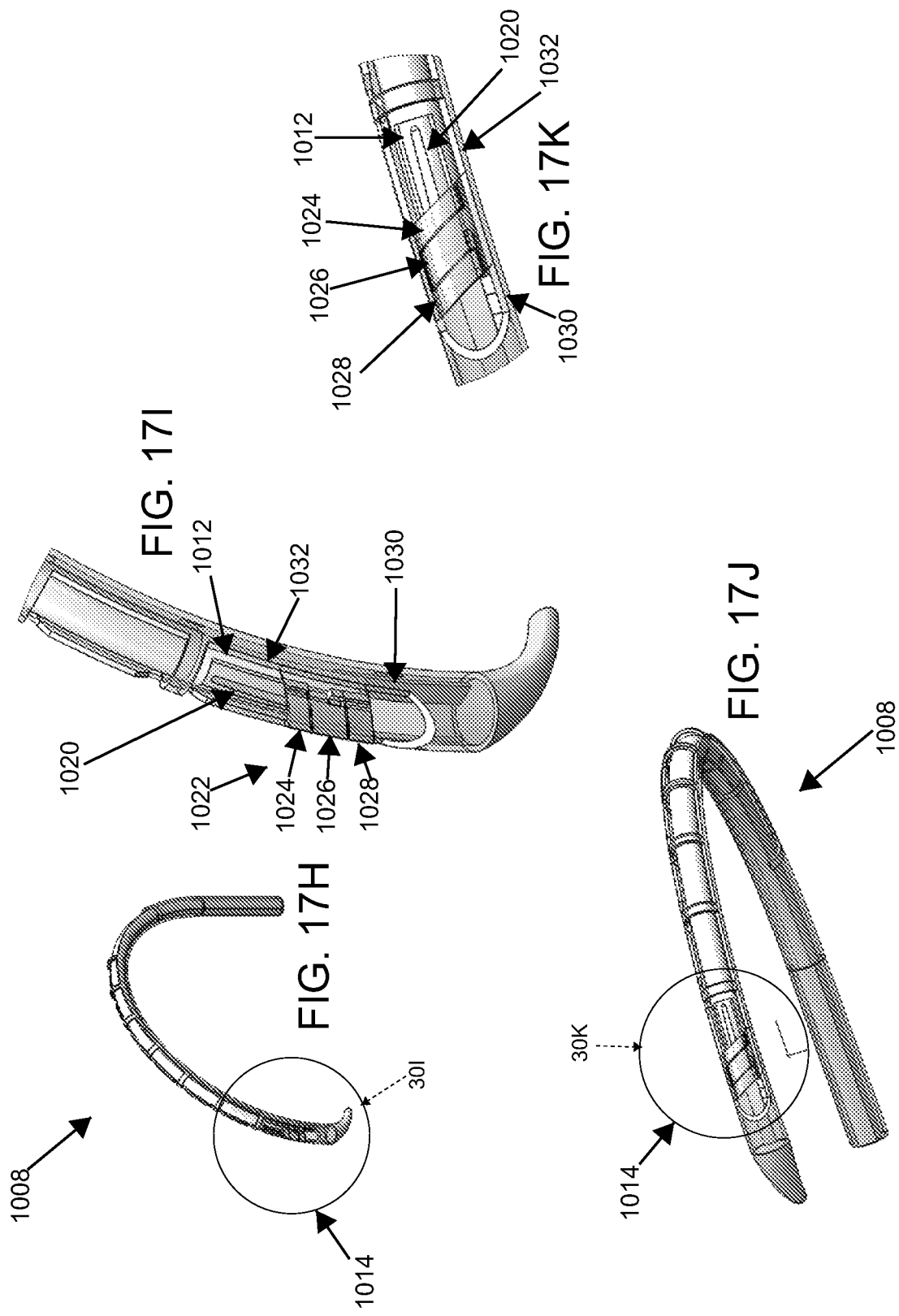

DEVICES AND METHODS FOR ANCHORING TISSUE

CROSS-REFERENCE TO RELATED APPLICATIONS

This application is a U.S. National Phase application under 35 U.S.C. §371 of International Application No. PCT/US2011/050331, filed Sep. 2, 2011, which designated the United States and which claims the benefit of U.S. Provisional Application No. 61/380,182, filed Sep. 3, 2010, the disclosures of all of which are hereby incorporated in their entirety.

BACKGROUND

Blood returning to the heart from the peripheral circulation and the lungs generally flows into the atrial chambers of the heart and then to the ventricular chambers, which pump the blood back out of the heart. During ventricular contraction, the atrio-ventricular valves between the atria and ventricles, i.e. the tricuspid and mitral valves, close to prevent backflow or regurgitation of blood from the ventricles back to the atria. The closure of these valves, along with the aortic and pulmonary valves, maintains the uni-directional flow of blood through the cardiovascular system. Disease of the valvular apparatus can result in valve dysfunction, where some fraction of the ventricular blood regurgitates back into the atrial chambers.

Traditional treatment of heart valve stenosis or regurgitation, such as mitral or tricuspid regurgitation, involves an open-heart surgical procedure to replace or repair the valve. Current accepted treatments of the mitral and tricuspid valves include: valvuloplasty, in which the affected leaflets are remodeled to perform normally; repair of the chordae tendineae and/or papillary muscle attachments; and surgical insertion of an "annuloplasty" ring, which requires suturing a flexible support ring over the annulus to constrict the radial dimension. Other surgical techniques to treat heart valve dysfunction involve fastening (or stapling) the valve leaflets to each other or to other regions of the valve annulus to improve valve function.

BRIEF SUMMARY

Described herein are devices and methods that involve attachment sites, including implants with multiple coupled anchors. The anchors may be secured to tissue using a multi-opening guide tunnel that is configured to releasably retain one or more portions of the implant located between two anchors, such as a tether component that attaches the anchors. The releasable retention of one or more interconnecting portions of the implant provides additional stabilization for the delivery tool until the implant is secured to the tissue. The multi-opening guide tunnel permits securement of the multiple anchors without requiring repositioning of the guide tunnel for each anchor. In some embodiments, the multi-opening guide tunnel comprises disengageable wall segments between the openings of the guide tunnel, which provide structural support and column strength in a region of the guide tunnel that would buckle or collapse due to the number of openings and their configuration.

In some embodiments, a system for use in a patient is provided, comprising an outer catheter, which comprises a passageway with a proximal end, a distal end, a longitudinal axis and two or more outer openings, and at least one releasable retaining structure located between the two or more outer openings. At least one releasable retaining structure may be adapted to open a release channel between two or more outer openings. In some instances, at least two of the two or more outer openings are two adjacent outer openings with a separation distance less than a maximum dimension of one of the two adjacent outer openings, and at least one releasable retaining structure is located between the two adjacent outer openings. In some variations, two or more outer openings are longitudinally spaced along a longitudinal length of the outer catheter, and may be configured for passage of a tissue anchor. At least one releasable retaining structure may be configured to retain a tether attached to the tissue anchor, and is optionally an outer wall structure of the outer catheter. The outer catheter may comprise at least three outer openings, and optionally at least two releasable retaining structures. The system may further comprise an inner catheter slidably located in the passageway of the outer catheter, and sometimes may further comprise an alignment interface between the outer catheter and the inner catheter. The alignment interface may comprise a rail, which may be a metallic material and/or may be secured to the outer catheter at two or more securing sites. The outer catheter may also further comprise a curved configuration having a lesser curvature and a greater curvature, and in some embodiments, two or more openings may be generally located along the greater curvature of the outer catheter. The outer catheter may also comprise an atraumatic tip. The catheter may further comprise at least one radio-opaque structure located between the two or more outer openings. The inner catheter may comprise an inner opening and wherein the inner guide and outer guide are configured to permit positioning of the inner opening at two or more outer openings. In some embodiments, at least one releasable retaining structure comprises a locking passage. The at least one locking element may be configured for removable positioning in the locking passage of at least one releasable retaining structure, and at least two releasable retaining structures with locking passages are both optionally configured for removable positioning by one of the at least one locking elements.

In other embodiments, an implant delivery system is provided, comprising a catheter body which comprises a proximal end, a distal end, a longitudinal lumen therebetween, a lumenal surface, an ablumenal surface, and at least one implant delivery opening in communication with the longitudinal lumen and located between the luminal surface and the ablumenal surface, and at least two longitudinally-spaced retention members located distal to the proximal end of the catheter body. In some instances, at least two longitudinally-spaced retention members are located within the longitudinal lumen, or within the at least one implant delivery opening. At least two longitudinally-spaced retention members may have a transverse orientation with respect to the longitudinal lumen. In some embodiments, at least two longitudinally-spaced retention members are movable retention members, which may be rotatable or flexible retention members. The movable retention members may each comprise a through lumen. The implant delivery system may further comprise a first anchor coupled to a tether, and in some instances at least two longitudinally-spaced retention members are configured to retain the tether.

In one embodiment, an implant may comprise an anchor for securing a tether to human tissue. The anchor may comprise a shape memory wire body having an unconstrained curved elongate form with a single loop, the elongate form generally following a curved arcuate path in a single turning direction. The anchor may have two legs arranged to diverge away from each other. The legs have a generally non-constant radius of curvature, and a straight distal tip.

Some embodiments of an implant delivery system may comprise a multi-window catheter for the deployment of tissue anchors into human tissue. The improved multi-window catheter has an outer shaft with a multiple windows, an inner shaft for regulating the use of the windows and a lumen therethrough for slidably receiving an anchor deployment catheter. The multi-window catheter may comprise two or more adjacent releasable flaps on a distal section of the outer shaft. The adjacent releasable flaps may be configured to allow the deployment of two anchors in close proximity to each other.

BRIEF DESCRIPTION OF THE DRAWINGS

The structure and method of using the invention will be better understood with the following detailed description of embodiments of the invention, along with the accompanying illustrations, in which:

FIGS. 5 and 6 are frontal views of another variation of an anchor;

FIG. 7 is a superior view of the anchor of FIG. 5 from the line C-C;

FIG. 8 is a side elevational view of the anchor from FIG. 5 from the line D-D;

FIG. 12 is a frontal view of the delivery catheter of FIG. 11, and

FIGS. 13 and 14 are side and bottom views, respectively, of a portion of the delivery catheter of FIG. 11;

FIG. 15A depicts one embodiment of a multi-opening guide tunnel; FIG. 15B depicts the multi-opening guide tunnel of FIG. 15A with its latches unlocked and separated from the body of the guide tunnel.

FIGS. 16A to 16H are various perspective views of one embodiment of a multi-opening guide tunnel; and FIG. 17A is a side elevational view of another variation of a guide tunnel; FIG. 17B is a detailed view of the distal portion of the guide tunnel from FIG. 17A; FIG. 17C is an enlarged view of the distal window as annotated in FIG. 17B; FIG. 17D is a cross-sectional view of the guide tunnel taken along the lines 17D-17D; FIG. 17E is a perspective view of the guide tunnel of FIG. 17A, where the guide tunnel has been rotated around the longitudinal axis; FIG. 17F is a detailed view of the distal portion of the guide tunnel from FIG. 17E; FIG. 17G is a cross-sectional view of the guide tunnel taken along the lines 17G-17G; FIG. 17H is a superior perspective view of the distal portion of the guide tunnel from FIG. 17A; FIG. 17I is a detailed view of the distal portion of the guide tunnel from FIG. 17H; FIG. 17J is another superior perspective view of the distal portion of the guide tunnel from FIG. 17A; and FIG. 17K is a detailed view of the distal portion of the guide tunnel from FIG. 17I.

DETAILED DESCRIPTION

Figure 1:
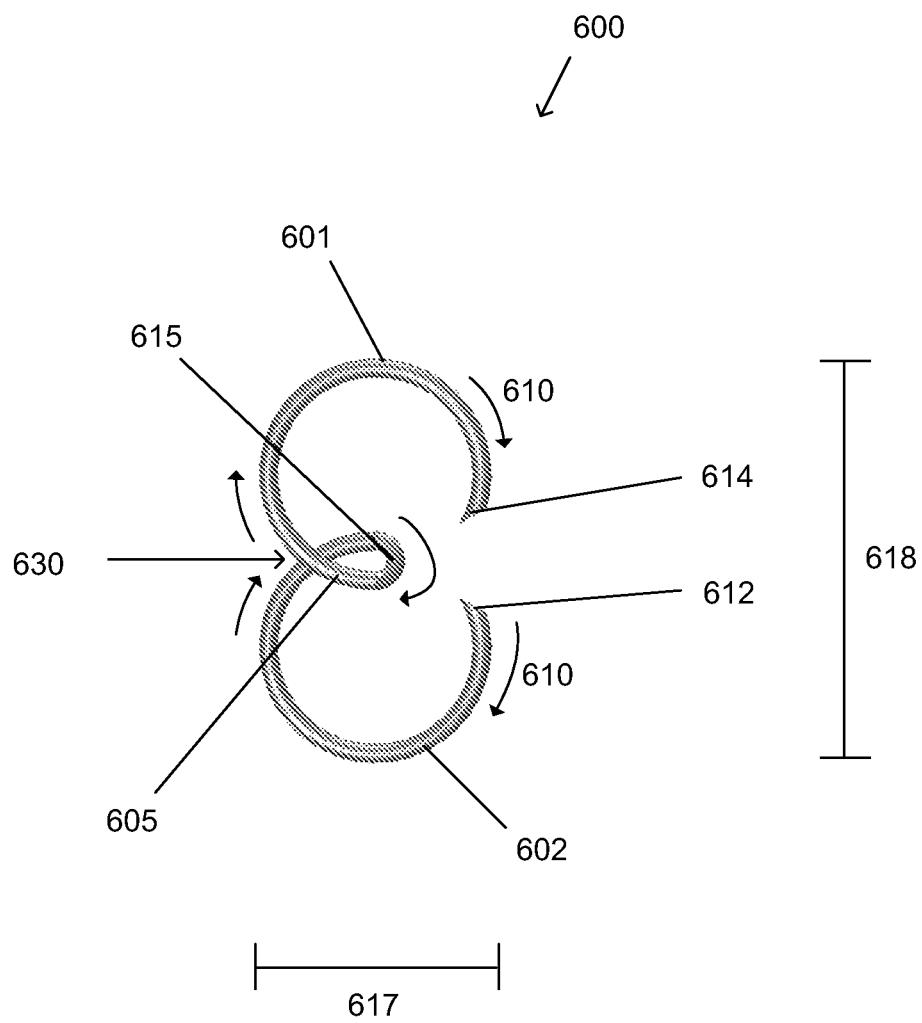
FIG. 1 is a perspective view of an anchor as described herein.

Although a number of surgically implanted ventricular devices and procedures, such as the implantation of an annuloplasty ring or edge-to-edge leaflet repair, are available for treating valvular dysfunction, each procedure presents its own set of risks to the patient or technical challenges to the physician. For example, the ability to accurately and reliably position a cardiac implant during a beating heart procedure, whether by open chest or minimally invasive access, remains elusive to the average practitioner. In particular, the percutaneous or transvascular implantation of a ventricular device described herein poses a significant challenge due to the instability from the wall motion of a beating heart.

Devices, systems and methods of the instant invention are generally used to reshape atrio-ventricular valves or myocardium to improve hemodynamic performance. The implantation procedures are preferably transvascular, minimally invasive or other "less invasive" surgical procedures, but can also be performed with open or limited access surgical procedures. When used for treatment of a cardiac valve dysfunction, the methods generally involve positioning one or more anchor delivery devices at a target site using a guide tunnel, delivering a plurality of slidably coupled anchors from the delivery device(s), and drawing the anchors together to tighten the annulus. The devices include an elongate catheter with a housing at or near the distal end for releasably housing one or more anchors, as well as guide devices for facilitating advancement and/or positioning of an anchor delivery device. The devices may be positioned such that the housing abuts or is close to valve annular tissue, such as the region within the upper left ventricle bound by the left ventricular wall, a mitral valve leaflet and chordae tendineae. Self-securing anchors having any of a number of different configurations may be used in some embodiments.

"Anchors," as described herein refer to tissue anchors made of a shape memory material. The anchors may comprise C-shaped or semicircular hooks, curved hooks of other shapes, straight hooks or barbed hooks. In an embodiment, anchors may comprise two tips that curve in opposite directions upon deployment, forming two intersecting semi-circles, circles, ovals, helices or the like. In some embodiments, the tips may be sharpened or beveled. In some embodiments, the anchors are self-deforming. By "self-deforming" it is meant that the anchors are biased to change from a constrained shape to a unconstrained shape upon release of the anchors from a restraint. Such self-deforming anchors may change shape as they are released from a housing or deployed from a lumen or opening to enter annular tissue, and secure themselves to the tissue. Self-deforming anchors may be made of any suitable material such as spring stainless steel, or super-elastic or shape-memory material like nickel-titanium alloy (e.g., Nitinol).

In some embodiments, anchors may comprise one or more bioactive agents, including biodegradable metals and, polymers. In another aspect, the anchors may comprise electrode components. Such electrodes, for example, may sense various parameters including but not limited to impedance, temperature and electrical signals. In other aspect, such electrodes may be used to supply energy to tissue at ablation or sub-ablation amounts.

In an embodiment, an anchor may be a flexible anchor having two curved legs that cross in a single turning direction to form a loop, wherein the legs are adapted to penetrate tissue. FIG. 1 illustrates one example of an anchor as described herein. In FIG. 1, the anchor 600 has curved legs 601, 602 and a loop region 605. The legs and loop region all have a single turning direction, indicated by the arrows 610.

The single turning direction describes the curvature of the legs and loop region of the anchor, including the transitions between the legs and loop region. For example, in FIG. 1 the limbs of the anchor and the loop region define a single direction of curvature when following the length of the anchor from tip to tip. Starting at the tip 612 of the lower leg 602 of the anchor shown in FIG. 1, the anchor curves only in one direction (e.g., to the right) from the tip of one leg of the anchor 612, through the loop region 605, to the tip of the other leg 614. Another way to describe the single turning direction of the anchor is to imagine a point traveling along the anchor from the tip of one leg to the tip of the other end. As the point moves along the length of the anchor down the legs and loop region, the point turns only one direction (e.g., right/left or clockwise/counterclockwise). The angle that the point turns (the turning angle, from which the point is deflected from continuing straight ahead) anywhere along the length of the anchor can be of any appropriate degree, i.e., between 0° and 180°. The anchor is generally continuously connected from leg-tip to leg-tip, as shown in FIG. 1.

Anchors having a single turning direction may bend or flex more than anchors having more than one turning direction. For example, anchors having more than one turning direction typically have one or more surfaces (e.g., abutment surfaces) that inhibit the collapse and/or expansion of the anchors, as described further below.

The anchor shown in FIG. 1 is in a deployed configuration, in which the legs of the anchor are expanded. The legs (which may also be referred to as arms) of this anchor 601, 602 are curved and thus form a semicircular or circular shape on either side of the loop region 605. The legs may be less uniformly curved, or un-curved. For example, the legs may form elliptical or semi-elliptical shapes, rather than circular/semicircular shapes. In some variations, the legs are not continuously curved, but may contain regions that are uncurved. In some variations, the anchor may comprise sharp bends.

The anchors described herein may have a deployed configuration and a delivery configuration. The deployed configuration is the configuration that the anchor assumes when it has been deployed into the tissue. The anchor may be relaxed in the deployed configuration. The delivery configuration is any configuration in which the anchor is prepared for delivery. In some variations, the arms are compressed in the delivery configuration, so that the anchor has a smaller or narrower profile. The narrower profile may allow the anchors to be delivered by a small bore catheter. For example, anchors in a delivery configuration may fit into a catheter having an I.D. of about 0.5 mm to about 3.0 mm. In some variations, the anchor may be used with a delivery device having an I.D. of about 1 mm.

The ends of the legs 612, 614 are configured to penetrate tissue, so that the legs of the anchor may pass into the tissue when the anchor is deployed, as described more fully below. In some variations, the leg ends are blunt, or rounded. Blunt or rounded ends may still penetrate tissue. In some variations, the tips of the leg ends are sharp, or pointed, as shown in FIG. 1. In FIG. 1, the leg ends are beveled so that they have a sharp end. In some variations, the ends of the legs may include one or more barbs or a hooked region (not shown) to further attach to the tissue.

The loop region 605 may also be referred to as an eye, eyelet or eye region. In the exemplary anchor shown in FIG. 1, the loop region comprises a single loop that is continuous with the legs 601, 602, and lies equally spaced between the two legs. For example, both legs 601, 602, cross once to form the loop region having a single loop. In some variations, the legs have different lengths or shapes, and the loop region is not centered between equal-sized legs. In some variations, the loop region has more than one loop. For example, the loop region may be formed by more than one complete turn. Thus the loop region may comprise a helical shape having more than one loop (e.g., two loops, three loops, etc.).

The loop region may be of any appropriate size, and may change size based on the configuration of the anchor. For example, when the anchor is in a deployed configuration, the loop region may be larger (e.g., wider) than when the anchor is in a delivery configuration. In some variations, the loop region is smaller when the anchor is in a collapsed configuration, thus, the loop region may be of any appropriate shape, and may also change shape based on the configuration of the anchor. For example, the loop region may be more elliptical (e.g., narrower) in a delivery configuration, or more rounded. The central portion of the anchor loop may define the width of the anchor when constrained.

The position of the legs may be changed depending on the configuration of the anchor. For example, the legs may be expanded or collapsed. The expansion of the legs may increase the width and/or length of the anchor, for example, such that the width and/or length of the anchor is substantially larger than the dimensions of the loop. The legs 601, 602 may contact each other by meeting at a point of contact 630. In some variations, the legs 601, 602 cross each other without contacting. In some variations, the legs contact each other, so that the loop 605 is a closed region. In some variations, the legs are attached to each other at the point of contact 630. In some variations, one of the legs may pass through a passage (e.g., a hole) in the other leg.

The anchor may also have a thickness. For example, the anchor shown in FIG. 1 is substantially planar, meaning that the legs typically move in a single plane (e.g., the plane parallel to the page). The anchor in FIG. 1 is formed of a substantially cylindrical wire-like member, and the anchor has a thickness that is approximately twice the thickness of the wire-like member, because the legs cross over each other at point 630. The legs or body of the anchor (including the loop region) may also be at least partially hollow. For example, the anchor may be formed from a tube, or may include a tube region. Thus, the anchor may include one or more hollow regions that may allow tissue ingrowth, or may be used to hold additional materials (e.g., drugs, electronics, etc.). In some variations, the hollow region of the anchor may comprise drugs that may be eluted (e.g., time release drugs). Overall, the anchor may be of any appropriate thickness. Furthermore, in some variations, the legs may move in any appropriate direction, including directions that are different from the plane in which the legs lie. For example, in one variation, the legs move in a corkscrew fashion (e.g., from a delivery configuration to a deployed configuration).

In FIG. 1, the opening formed by the loop region creates a passage through the plane of the anchor, so that material (e.g., a tether) may pass through the loop, and therefore through the plane formed by the anchor legs and loop region. In this variation, the legs move mostly within this plane. In some variations, the anchor does not form a single plane as shown in FIG. 1, but instead, the legs extend in a single turning direction, and also extend up or down from the plane of the figure shown in FIG. 1. Furthermore, the loop region may also face a direction that is not parallel to the plane formed by the anchor. For example, the loop region may face a direction that is parallel to the plane formed by the legs. Thus, a material passing through the loop region may pass through in a direction that is not perpendicular to the plane formed by the rest of the anchor. The legs and/or the loop region may be twisted so that they extend from a plane that is not the same as the plane formed by the rest of the anchor.

Figure 2:
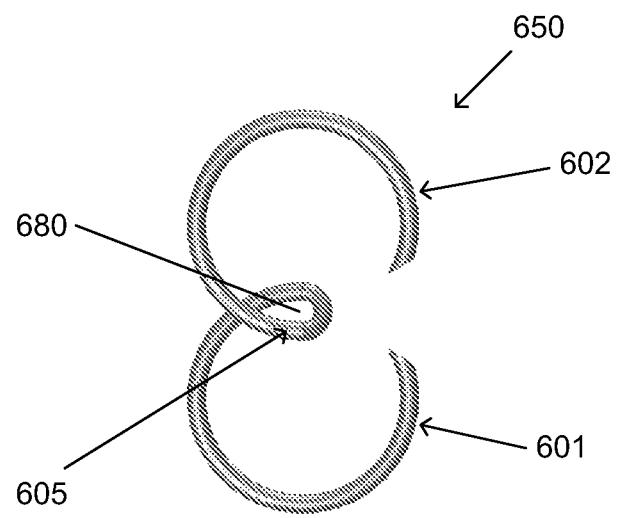
FIGS. 2 and 3 show perspective views of the anchor of FIG. 1 in an expanded and compressed state, respectively.
Figure 3:
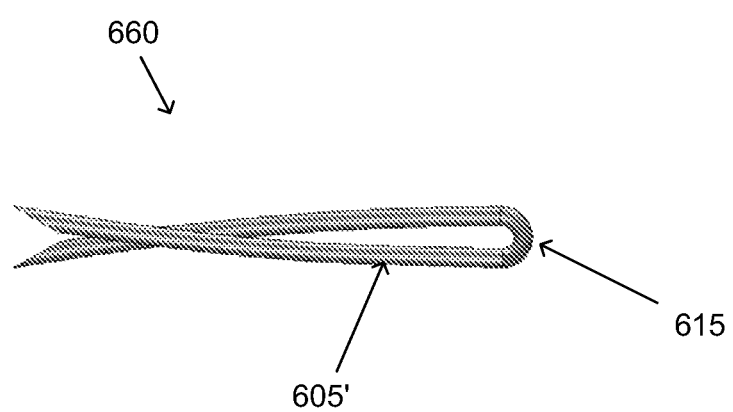

An anchor may be made of a single material, or it may be formed of many materials. In one variation, the anchor is made of a single piece of material. For example, the anchor may be formed from a linear material (e.g., a wire) that is formed into the desired shape (e.g., the deployed configuration). In some variations, the anchor is cut or etched from a sheet of material, (e.g., Nitinol). In some variations, the anchor includes different regions that are connected or joined together. These different regions may be made of the same material, or they may be made of different materials. The different regions may include regions having different physical or material properties, such as material strength, flexibility, ductability, elasticity, and the like. For example, the loop region of the anchor may comprise a material having a different (e.g., a decreased or increased) stiffness compared to the leg regions. In FIG. 1, part of the loop region 605 is a segment 615 that is joined to the segments forming the legs 601, 602. In this example, the central portion 615 of the loop region 605 is less flexible than the legs 601, 602, so that it is less likely to deform (e.g., requires more energy) than the adjacent leg regions, and may maintain an approximate shape (e.g., an elliptical shape, as shown in FIGS. 1-3) of the loop region.

An anchor may be made of (or may contain a region or coating of) a biodegradable or bioabsorbable material. Biodegradable portions of the anchor may allow time-controlled changes in the mechanical or biochemical properties of the anchor and in the interaction of the anchor with the tissue. For example, an outer layer of the anchor may dissolve over time, rendering the anchor thinner and more flexible. Thus, an anchor may be initially quite thick (e.g., providing an initial strength or stiffness), but after insertion into the tissue, the outer layer may dissolve or be removed, leaving the anchor more flexible, so that it can better match the tissue compliance.

In some variations, a region having an enhanced flexibility creates a spring or hinge region that can enhance or limit the overall flexibility of the anchor or a region of the anchor. This can, in turn, affect the ability of the anchor to change configurations between a deployed and a delivery configuration. As described further below, a hinge or spring region may be used to enhance the effectiveness of the anchor during cyclic (e.g., repetitive) loading of a tissue into which an anchor has been inserted.

Anchor Configurations

The anchors described herein are generally flexible anchors, and may transition between a deployed configuration and one or more compressed or expanded configurations. The deployed configuration may also be referred to as a relaxed configuration. As mentioned above, the delivery configuration may be a compressed configuration (as shown in FIG. 3) or an expanded configuration (as shown in FIG. 1). The anchor may by compressed or expanded to different amounts, so that there may be many expanded or compressed configurations.

FIGS. 2 and 3 show examples of an anchor in a deployed configuration and a delivery configuration, respectively. When the anchor is in the deployed configuration 650, as shown in FIG. 2, the legs 601, 602 are typically expanded radially, and the loop region 605 has an opening 680 through which a material (e.g., a tether) may be attached or may pass. This deployed configuration is the configuration that this variation of the anchor assumes when external forces on the anchor are minimal.

At least a portion of the anchor comprises an elastic or super-elastic material, such as a metal, alloy, polymer (e.g., rubber, poly-ether ether ketone (PEEK), polyester, nylon, etc.) or some combination thereof that is capable of elastic or super-elastic recovery from deformation. For example, the anchor may comprise a Nickel-Titanium Alloy (e.g., Nitinol), or a region that is a rubber or polymeric material. In some variations, the anchor may comprise a material having a shape memory. In some variations, the anchor may comprise a bioabsorbable and/or biodegradable material (e.g., polymers such as polylactic acid (polylactide), poly-lactic-co-glycolic acid (poly-lactido-co-glycolide), polycaprolactone, and shape memory polymers such as oligo($\epsilon$-caprolactone)diol and crystallisable oligo($\rho$-dioxanone)diol, etc.).

When force is applied to the anchor, or to a tissue into which the anchor is embedded, the anchor may flex or bend and thereby absorb some of the energy applied, and change the configuration of the anchor. For example, the anchor may be compressed or expanded from a resting position. In particular, the anchor may be compressed from a deployed configuration such as the one shown in FIG. 2 into smaller delivery configuration such as the one shown in FIG. 3.

In FIG. 3, the anchor has been compressed into a delivery configuration by drawing the ends of the legs back so that the anchor has a smaller profile with a stored potential energy that can revert the anchor back into the deployed configuration (e.g., the anchor may be self-deforming). In this variation of the delivery configuration, the anchor profile is much narrower than in the deployed configuration. The legs of the anchor have been extended (reducing their curve), enlarging or expanding the opening formed by the loop region 605. In this example, the loop region remains narrow and elliptical, because one portion of the loop region 615 is less flexible than the other portions of the loop region and the leg regions, as described above. This less flexible portion of the loop, or loop size limiter 615, limits the width that the loop region may expand to, and comprises a sub-region of the loop region that is less flexible than other regions of the anchor (e.g., the legs). In some variations, the loop size limiter region is flexible. In some variations, the loop size limiter region comprises an inflexible material. In some variations, the loop region expands as the anchor (e.g., the anchor legs) is compressed into a delivery configuration, so that the overall size of the loop region 605' increases both in width and length.

In some variations, the anchor has a delivery configuration in which the arms of the anchor may be radially expanded from their position in the deployed configuration.

The anchor 600 may be compressed from the deployed configuration into a delivery configuration by any appropriate method. For example, the legs of the flexible anchor 601, 602 may be drawn back into the delivery configuration as shown in FIG. 3, and held until the anchor is to be deployed into a tissue. Because the anchor comprises an elastic or super-elastic material, the anchor will typically store energy used to change the anchor from the delivery configuration to the deployed configuration. Upon releasing the anchor from the delivery configuration, the stored energy is released, and the anchor expands into the deployed configuration, as shown in FIG. 2. When the anchor is compressed into a delivery configuration, this energy may be used to help drive the legs of the anchor into the tissue, and may draw the anchor into the tissue. Thus, the anchor may be self-expanding, self-deforming, or self-securing. In some variations, deployment of the anchor into the tissue drives the legs into tissue in a curved pathway, helping to pull and secure the anchor into the tissue, as described more fully below.

In FIGS. 2 and 3, the deployed anchor has a much bigger leg span than the compressed anchor. In other words, the distance between the legs of the anchor in the deployed state 650 is larger than the distance between the legs of the anchor in the compressed state 660. In some variations, the ratio of the distance between the legs in the compressed state versus the distance between the legs in the deployed state is between about 1:2 to about 1:20. In some variations, the ratio of the distance between the legs in the compressed state versus the distance between the legs (e.g., at the ends of the legs) is between about 1:2 to about 1:10. In some variations, the ratio of the distance between the legs in the compressed state versus the distance between the legs (e.g., at the ends of the legs) is between about 1:8 to about 1:9. For example, the ratio of the distance between the legs in the compressed state of FIG. 3 versus the distance between the legs in the deployed state in FIG. 2 is approximately 1:6. The wide span of the deployed anchor may allow the anchor to distribute loading of the anchor over or wide area within the tissue matrix, preventing high local stresses on the tissue by distributing stresses on the tissue from the anchor over a larger area of the tissue. Distributing the forces over a larger area may prevent damage to the tissue, and may allow better attachment and healing.

As described above, the material moduli, shapes and sizes of different regions of the anchor may be selected so that the compressed and/or expanded shape of the anchor may be controlled. For example, in FIG. 3, the width of the compressed anchor is limited by the loop size limiter region 615 as described above. The forces required to compress or expand the anchor from the deployed configuration into the delivery configuration may be affected by the overall size and/or shape of the anchor, including the thickness of the legs and loop region.

As briefly described above, the anchor may be of any appropriate size or dimension. The anchor may have a width 617, length 618 and a thickness. For example, the length of the anchor may be measured as the span of the legs 618 as shown in FIG. 1. In one variation, the width of the anchor 617 in the deployed configuration may be less than 5 millimeters (mm) wide. In some variations, the anchor is between about 1 mm wide and about 9 mm wide in the deployed configuration. In some variations, the anchor is about 4 mm wide in the deployed configuration. Furthermore, the anchor may comprise any appropriate thickness or range of thicknesses. In some variations, the thickness of the anchor varies over the different regions (e.g., legs and loop region). In general, the anchor may comprise a thickness of between about 0.12 mm to about 0.75 mm. In one variation, the anchor is about 0.4 mm thick. In some variations, a portion of the loop region is thicker than a leg region of the anchor. For example, the loop size limiter region may be thicker than the leg regions, so that the leg regions are more readily bent than the loop region, as described above. The length 618 of the deployed anchor may be from about 1 mm to about 20 mm long. In some variations the deployed anchor is about 10 mm long.

Anchors may be fabricated by any appropriate method. For example, an anchor may be made by working or shape-forming a material (e.g., an alloy or metal). In some variations, the anchor may be fabricated from a wire or wires. The examples of anchors shown in FIGS. 1 and 2 are all rounded, wire-like anchors. However, anchors may have flat or flattened sides. In some variations, the anchor or a part of the anchor is fabricated by cutting, stamping, or etching some or part of the anchor from a material. For example the anchor can be formed by cutting it out of a Nitinol sheet using a laser, EDM, or Photoetching. In some variations, the anchor or a part of the anchor is fabricated by molding or extrusion techniques. The entire anchor (e.g., legs and loop region) may be formed from a single continuous piece, or the anchor may be formed by attaching different component pieces together. Thus, an adhesive or other joining material may be used to connect different components of the anchor. The components may also be joined by welding, brazing or soldering.

Furthermore, an anchor may be treated or coated in any appropriate manner. In some variations, the anchor is sterilized. For example, an anchor may be irradiated, heated, or otherwise treated to sterilize the anchor. Sterilized anchors may be packaged to preserve sterility. In some variations, an anchor may be treated with a therapeutic material (e.g., a medicinal material such as an anti-inflammatory, an anticoagulant, an antiproliferative, a pro-proliferative, a thrombo-resistant material, a growth hormone, etc.) to promote healing. For example, the anchor may be coated with Vascular Endothelial Growth Factor (VegF), Fibroblast Growth Factor (FGF), Platelet-Derived Growth Factor (PDGF), Transforming Growth Factor Beta (TGFbeta, or analogs), insulin, insulin-like growth factors, estrogens, heparin, and/or Granulocyte Colony-Stimulating Factor (G-CSF). In some variations, the anchor may comprise pockets of material for release (e.g., medicinal materials). In some variations, the anchors may be coated with a material to promote adhesion (e.g., tissue cements, etc.) In some variations, the anchors may comprise a material to assist in visualizing the anchor. For example, the anchor may comprise a radiopaque material, or other contrast-enhancing agents (e.g., these agents may depend upon the material from which the anchor is made, and the imaging modality used). For example, the anchor may be coated with a metal, such as gold, aluminum, etc. The anchor may also comprise surface treatments, including texturing (e.g., by ion beam etching, photoetching, etc.), tempering (e.g., thermal or photo tempering), or the like. Additional examples of appropriate surface treatments may include electropolishing, chemical etching, grit or bead blasting, and tumbling in abrasive or polishing media. Polymer coatings may include Teflon or polyester (e.g., PET). In some embodiments the anchors may be electropolished.

Coatings may be used to elute one or more drugs, as described above. For example, an outer layer may comprise a drug (or other dissolvable or removable layer) that exposes another layer (e.g., another drug layer) after it dissolves or is removed. Thus, the anchor may controllably deliver more than one drug in a controlled fashion. The release of a drug (or drug coating) may be affected by the geometry of the anchor, or the way in which the drug is arranged on or within the anchor. As described above, the anchor may comprise a hollow region or other regions from which a drug could be eluted. Thus, the anchor may include pits, slots, bumps, holes, etc. for elution of drugs, or to allow tissue ingrowth.

Different regions of the anchor may comprise different coatings. For example, the loop (or a portion of the loop) may include a lubricious coating, particularly in the region where the legs cross each other to form the loop. A lubricious coating (e.g., polytetrafluoroethylene (Teflon), silicones, hydrophilic lubricious coatings, etc.) in this region may help minimize friction when deploying the anchor and may give the anchor greater momentum during deployment.

Anchors may also include one or more sensors and/or telemetry for communicating with other devices. For example, an anchor may include sensors for sensing electrical potential, current, stress, strain, ion concentration, or for the detection of other compounds (e.g., glucose, urea, toxins, etc.). Thus, an anchor may include circuitry (e.g., microcircuitry) that may be powered by an on-board power source (e.g., battery) or by externally applied power (e.g., electromagnetic induction, etc.). Circuitry may also be used to analyze data. In some variations, the anchor may comprise telemetry (e.g., wireless telemetry) for sending or receiving data or instructions from a source external to the anchor. For example, the anchor may send data from a sensor to a receiver that is external to the subject. In some variations, the anchor may be used to controllably release material (e.g., drugs) into the tissue.

The anchor may also include one or more electrodes. Electrodes (e.g., microelectrodes) may be used to stimulate, or record from the tissue into which the anchor has been inserted. Thus, the anchor may be used to record electrical activity (e.g., cardiac electrical activity, muscle electrical activity, neuronal electrical activity, etc.). In some variations, the anchor can apply electrical stimulation to the tissue through the electrode. Stimulation or recording electrical activity may also be controlled either remotely (e.g., through telemetry) or by logic (e.g., control logic) on the anchor.

For example, the anchor may be deployed in nerves or other electrically active tissue so that electromagnetic or electrophysiological signals can be received or transmitted. In one variation, electrical signals are transmitted to a subject from (or through) an anchor for pain management or control. In one variation, the anchors may transmit signals to help control limp muscles (e.g., in stroke patients). Thus, an anchor may itself be an electrode. In one variation, an anchor is deployed into a tumor and energy (e.g., electrical energy) is applied through the anchor to ablate the tumor.

The anchors described herein may also include additional tissue-engaging features to help secure the anchors within the tissue, implant or graft. The anchors may include features to increase friction on the surface of the anchors, to capture tissue, or to restrict movement of the anchor and prevent pullout of the anchor.

For example, as described above, the ends of the anchor may comprise one or more barbs or hooks. In some variations, regions other than the ends of the legs (e.g., the body of the legs or loop region) may also include barbs or hooks for gripping. In one variation, a single curve having a tight radius may be present at the end of one or more of the anchor legs. The bend may hook into the tissue at the end of the leg like a long narrow fishhook.

Thus, the anchor may include regions of increased friction. In addition to the barbs described above, the anchor may also include tines, pores, holes, cut outs, or kinks. These features may increase friction and resistance to pullout, and (as described above) may also allow ingrowth of tissue that inhibits withdrawal of the anchor. The surface of the anchor may also be coated or textured to reduce friction or to increase interaction between the anchor and the tissue, implant, or other material.

Movement of the anchor may also be restricted (or guided) to enhance attachment with tissue or other materials. For example, although the anchor typically curves in a single turning direction, the radius of the single turning direction may vary over the length of the anchor. In general, the tighter the bend radius of a region of the anchor, the greater the resistance to unbending. For example, the anchor may incorporate one or more bends that have a smaller radius of curvature (e.g., is a tighter bend) than other regions of the anchor. In one variation, the anchor may comprise a plurality of relatively straight segments with intermediate, tight radius bends. An example of such a tight radius bend is depicted in FIG. 5 (e.g., width W1 of loop central region 404).

Figure 4:
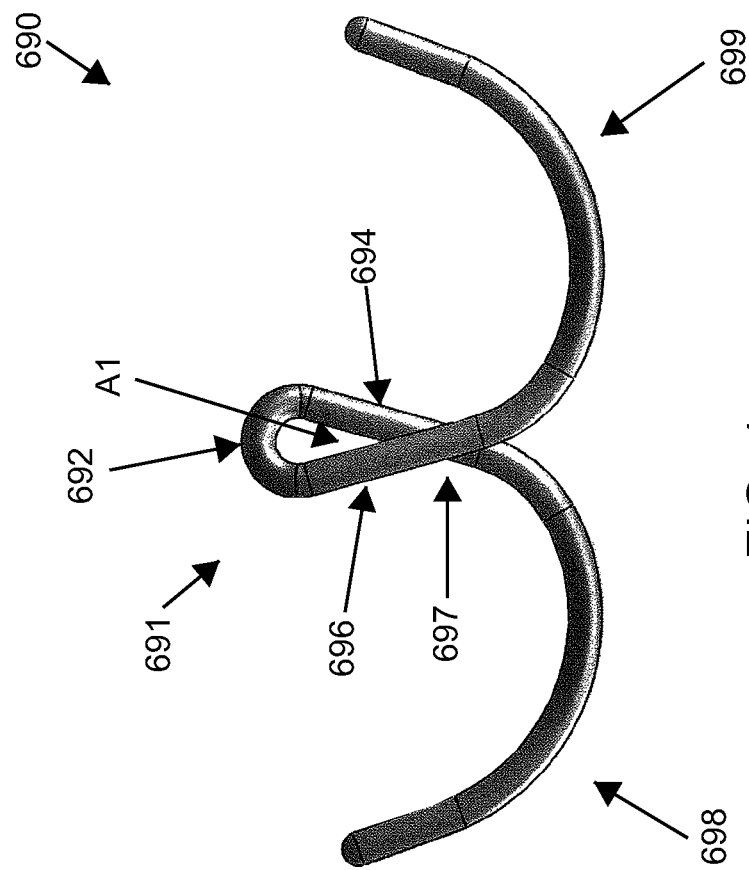
FIG. 4 depicts another variation of an anchor

As described previously, a loop region of an anchor may be of any appropriate size or geometry, which may change elastically or plastically during use from forces acting on the anchor, e.g. contraction and relaxation of the myocardium. In one variation, in the expanded deployed configuration, at least a length of the loop region may be formed from anchor segments that are substantially curved. In other variations, one or more segments of the loop region may be substantially straight. For example, the loop region 605 of the anchor 600 depicted in FIG. 1 may be formed from substantially curved anchor segments, i.e., the anchor segments that form the loop region have a turning angle, and/or may be approximated by a radius of curvature. FIG. 4 depicts one variation of an anchor 690 in a deployed configuration having a loop region 691 that is formed from a curved loop central segment 692, a first straight segment 694 extending from a first end of the loop central segment, and a second straight segment 696 extending from a second end of the loop central segment. The first and second straight segments 694, 696 may cross each other at an anchor crossover point 697 as they extend into first and second anchor legs 698, 699, respectively. A crossover angle A1 formed by the first straight segment 694, the crossover point 697, and the second straight segment 696 may be from about 5° to 170°, for example, from about 10° to about 45°, or about 30°. The crossover angle A1 may vary depending on the configuration of the anchor, e.g., the angle A1 may change as the anchor transitions from an undeployed configuration to a deployed configuration, and/or from a collapsed configuration to an expanded configuration.

Another variation of an anchor with a loop region formed by straight segments and curved segments in the deployed configuration is depicted in FIGS. 5-8. Anchor 400 has a loop region 402 that is formed from a curved loop central segment 404, a first straight segment 406 extending from a first end of the loop central segment, a first curved segment 408 extending from the first straight segment, a second straight segment 410 extending from a second end of the loop central segment, and a second curved segment 412 extending from the second straight segment. The first and second curved segments 408, 412 cross each other at an anchor crossover point 414 as they extend into first and second anchor legs 416, 418, respectively. Anchor legs 416, 418 follow a non-constant radius of curvature, such as the curvature of an oval or ellipse or other non-uniform arching shape. Thus the radius of curvature of the curved leg segments 416, 418 is not constant. This curvature may help to reduce the strain on the anchor legs resulting from muscle contraction or other mechanical forces the legs are exposed to after deployment into tissue. In some variations, the distal tips of each leg 416*dt*, 418*dt* may be straight. The straight distal tips 416*dt*, 418*dt* may help to provide improved deployment characteristics. Straight leg tips may allow the anchor legs to penetrate deeper into the target tissue before the leg tips diverge away from each other as the anchor is deployed into tissue. The non-constant radius of curvature may also contribute to deeper anchor penetration before the leg tips diverge. The crossover angle A2 formed by the first curved segment 408, the crossover point 414, and the second curved segment 412 may be from about 5° to 170°, for example, from about 10° to about 45°, or about 30°. The first straight segment 406 may be substantially parallel to the second straight segment 410 in the plane of the opening defined by the loop region 402. The distance D1 between the first straight segment 406 and the second straight segment 410 may be from about 0.02 inches to about 3.03 in, e.g., from about 0.0245 in to about 0.0260 in. The width W1 of the loop region 402 from the first side of the loop central portion 404 to the second side of the loop central portion may be from about 0.03 in to about 0.08 in, e.g., from about 0.05 in to about 0.07 in, or no more than 0.061 in. The thickness T1 of the loop central region 404 may be from about 0.01 in to about 0.02 in, e.g., from about 0.0170 in to about 0.0175 in, or about 0.0168 in. In some variations, the thickness T1 may be smaller than the thickness T2 of the legs. For example, the thickness T1 may be at most 0.0005 in smaller than the thickness T2 (e.g., where the thickness T2 is about 0.0173 in, the thickness T1 is no less than 0.0168 in).

While the loop region 402 of the anchor 400 comprises two straight segments and two curved segments, other variations may have three or more straight and curved segments. For example, a loop region may be formed from a first straight segment extending from a first end of a curved loop central region, a first curved segment extending from the first straight segment, a second straight segment extending from the first curved segment on one side, and a third straight segment extending from a second end of the curved loop central region, a second curved segment extending from the third straight segment, and a fourth straight segment extending from the second curved segment. The crossover point may be formed by the crossing over of any combination of straight or curved segments.

The anchor 400 may have any suitable geometry, dimensions, or proportions as desired. FIG. 6 depicts examples of dimensions that may be appropriate for the anchor 400. The thickness T2 of the legs may be from about 0.015 in to about 0.019 in, e.g., from about 0.017 in to about 0.0175 in. The thickness T2 may be constant along the length of the anchor legs and/or segments of the loop region, or may vary along the length of the legs and/or segments of the loop region. The first and second anchor legs 416, 418 may have curved and/or straight portions. The curved portion of an anchor leg may have a curve that corresponds to an arc segment of an oval. For example, the curved leg segment 417 may be curved such that the midline 401 of the anchor leg corresponds to an arc segment of an oval with a major axis of about 0.15 in and a minor axis of about 0.11 in. The curvature of the curved leg segment 417 may approximate an arc segment of an oval with any suitable major and minor axis, e.g., the major axis may be from about 0.05 in to about 0.25 in, and the minor axis may be from about 0.06 in to about 0.21 in. An anchor leg may also have a straight portion, for example, the distal portion of the anchor legs of anchor 400 may have a straight leg segment 415. The length L1 of the straight leg segment 415 may be from about 0.04 in to about 0.6 in, e.g., from about 0.045 in to about 0.06 in, or 0.052 in. The height H1 from the bottom 421 of the curved leg segment of the anchor legs to the tip of the anchor leg ends 420, 422 may be from about 0.03 in to about 0.1 in, e.g., 0.05 in. The height H2 from the bottom 421 to the apex 423 of the loop region 402 may be from about 0.1 in to about 0.3 in, e.g., 0.223 in. The distance D2 along a line from the apex 423 to the projection of the anchor leg 416 on the line may be from about 0.05 in to about 0.3 in, e.g., from about 0.1 in to about 0.2 in, or 0.175 in. The first and second leg ends 420, 422 may have a radius of curvature from about 0.005 in to about 0.01 in, e.g., 0.008 in.

In some variations, different anchors may have expanded and/or deployed configurations such that height H1 and height H2 may vary with respect to each other. While height H1 of the anchor 400 is less than height H2, other anchors may have an expanded or deployed configuration where height H1 is equal to or greater than height H2. That is, in the deployed configuration, the anchor leg ends may curve back towards the loop region such that the leg ends are substantially co-linear with the apex of the loop region, or may extend past the apex of the loop region. For example, the leg ends in the deployed configuration of the anchor 650 in FIG. 2 extend past, e.g., beyond, the loop region, and the anchor 650 may have a height H1 that is greater than height H2. The ratio of height H1 to height H2 may vary as desired, and may range between about 1:10 to about 3:1, for example, about 1:5, 2:3, 4:5, 1:1, etc.

The height H3 of the loop region 402 is from the apex 423 to the crossover point 414, and may be from about 0.07 in to about 0.2 in, e.g., about 0.173 in. In some variations, the height H3 may be adjusted to help the anchor distribute forces that may be exerted on it, e.g., cyclic and/or dynamic loading forces from the tissue into which the anchor is inserted, stresses from the tissue, tensional forces that may result from cinching a tether inserted through the eyelet or loop region, etc. The height H3 of the loop region 4020 may also be adjusted ensure that when the anchor 400 is deployed and/or attached to tissue, a portion of the loop region 402 remains above the surface of the tissue. This may help ease the process of cinching a tether that may be threaded through the eyelets of multiple anchors, e.g., by reducing the frictional forces that oppose the cinching motion of the tether.

FIG. 7 is a top view of the anchor 400 from the line C-C. As depicted there, the first leg 416 and the second leg 418 may not be co-planar due to the turning of the anchor segments of the loop region 402. The first leg 416 may be in a first plane and the second leg 418 may be in a second plane, where the first and second planes are is substantially parallel to each other. This may be more clearly seen in FIG. 8, which is a side view of the anchor 400 from the line D-D. The first anchor leg 416 resides in the first plane and the second anchor leg 418 resides in the second plane, where the first and second planes are perpendicular to the surface of the paper. There may be a distance D3 between the first and second anchor legs (e.g., a distance between the first and second planes). The distance D3 may be from 0 in to about 0.01 in, e.g., from about 0.001 in to about 0.005 in. Referring back to FIG. 7, the loop central region 404 may connect between the first and second anchor legs, and form an angle A3 with the plane of the second anchor leg. The angle A3 may be from 5° to about 25°, e.g., 6°, or 18°.

Figure 9:
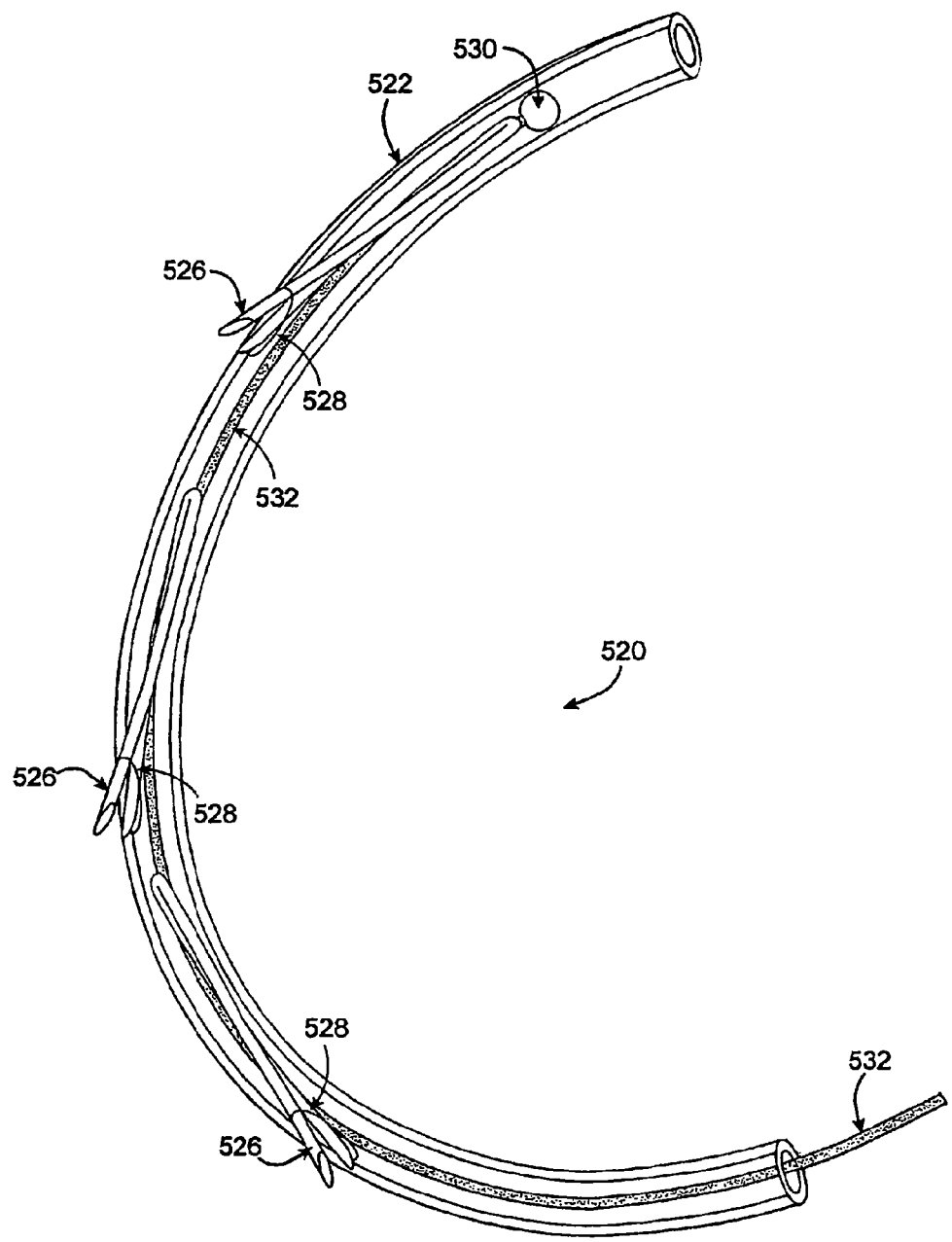
FIGS. 9 and 10 are perspective views of a distal portion of one embodiment of an anchor delivery catheter.
Figure 10:
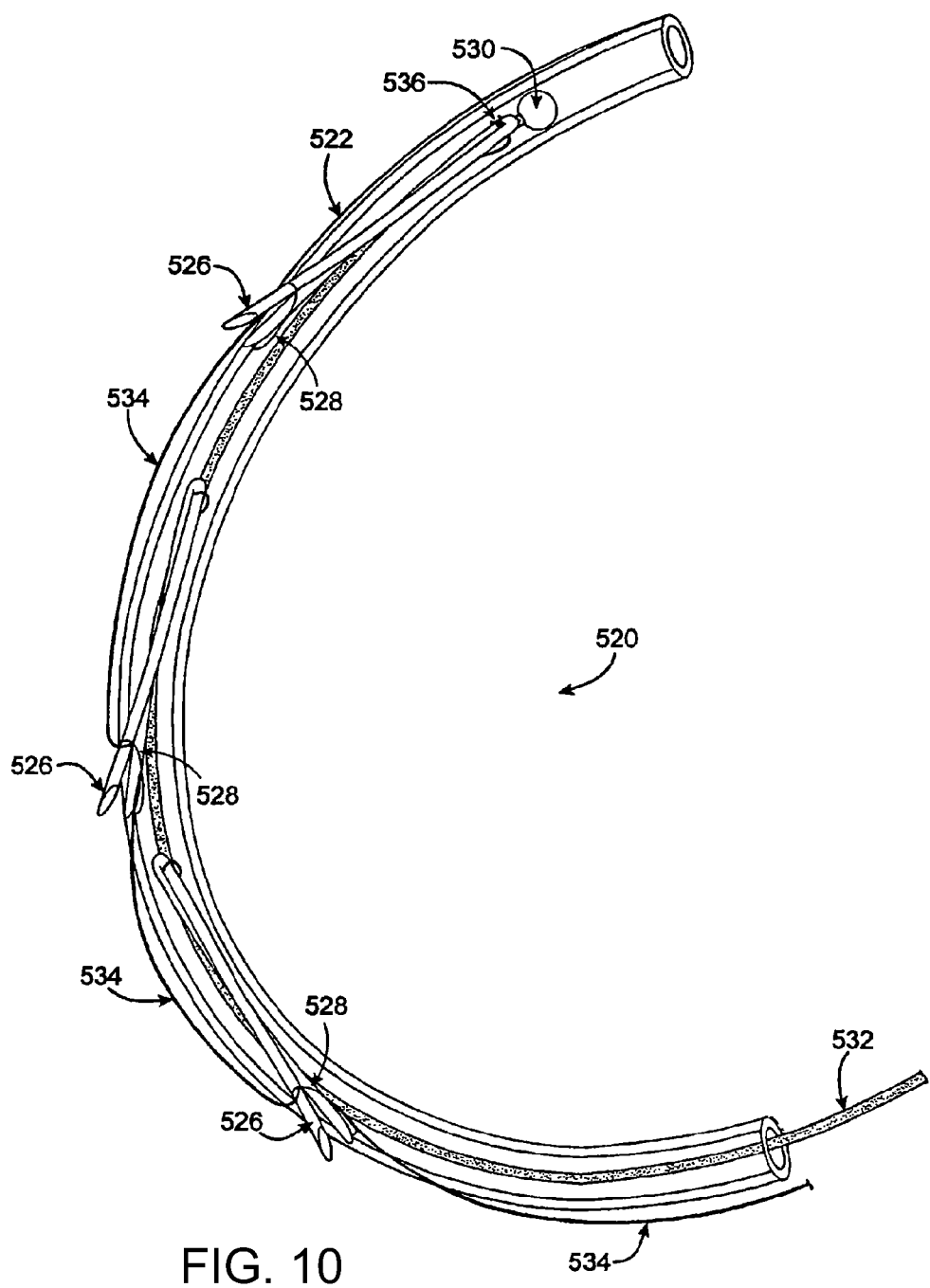

The catheters described herein, including tunnel catheter 148, may be formed of any of a number of different materials. Examples of suitable materials include polymers, such as polyether-block co-polyamide polymers, copolyester elastomers, thermoset polymers, polyolefins (e.g., polypropylene or polyethylene, including high-density polyethylene and low-density polyethylene), polytetrafluoroethylene, ethylene vinyl acetate, polyamides, polyimides, polyurethanes, polyvinyl chloride (PVC, fluoropolymers (e.g., fluorinated ethylene propylene, perfluoroalkoxy (PFA) polymer, polyvinylidenefluoride, etc.), polyetheretherketones (PEEKs), and silicones. Examples of polyamides include Nylon 6 (e.g., Zytel® HTN high performance polyamides from DuPont™), Nylon 11 (e.g., Rilsan® B polyamides from Arkema Inc.), and Nylon 12 (e.g., Grilamid® polyamides from EMS-Grivory, Rilsan® A polyamides from Arkema Inc., and Vestamid® polyamides from Degussa Corp.). In some variations, tunnel catheter 148 may be formed of multiple polymers. For example, a catheter may be formed of a blend of different polymers, such as a blend of high-density polyethylene and low-density polyethylene. While the wall of a catheter may be formed of a single layer, some variations of catheters may include walls having multiple layers (e.g., two layers, three layers). Furthermore, some variations of catheters may include at least two sections that are formed of different materials and/or that include different numbers of layers. Additionally, certain variations of catheters may include multiple (e.g., two, three) lumens. The lumens or walls may, for example, be lined and/or reinforced (e.g., with braiding or winding). The reinforcing structures, if any, may be metallic or comprise a non-metal or polymer having a higher durometer. In an embodiment, shown in FIGS. 9 and 10, a flexible distal portion of an anchor delivery device 520 includes a housing 522 configured to house multiple coupled anchors 526 and an anchor contacting member 530 coupled with a pull cord 532. Housing 522 may also include multiple apertures 528 for allowing egress of anchors 526. For clarity, delivery device 520 is shown without a tether in FIG. 9, but FIG. 10 shows that a tether 534 may extend through an eyelet, loop or other portion of each anchor 526, and may exit each aperture 528 to allow for release of the plurality of anchors 526. Anchors 526 may be relatively straight and may lie relatively in parallel with the long axis of delivery device 522. Anchor contacting member 530, which may comprise any suitable device, such as a ball, plate, hook, knot, plunger, piston, or the like, generally has an outer diameter that is nearly equal to or slightly less than the inner diameter of housing 522. Contacting member 530 is disposed within the housing, distal to a distal-most anchor 526, and is retracted relative to housing 522 by pulling pull cord 532. When retracted, anchor contacting member 530 contacts and applies force to a distal-most anchor 526 to cause release of that anchor 526 from housing 522 via one of the apertures 528. Contacting member 530 is then pulled farther proximally to contact and apply force to the next anchor 526 to deploy that anchor 526, and so on.

Retracting contacting member 530 to push anchors 526 out of apertures 528 may help cause anchors 526 to secure themselves to the tissue adjacent the apertures 528. Using anchors 526 that are relatively straighter/flatter configuration when undeployed may allow anchors 526 with relatively large deployed sizes to be disposed in (and delivered from) a relatively small housing 522. In one embodiment, for example, anchors 526 that deploy into a shape approximating two intersecting semi-circles, circles, ovals, helices, or the like, and that have a radius of one of the semi-circles of about 3 mm may be disposed within a housing 522 having a diameter of about 6 French (2.00 mm) and more preferably about 5 French (1.67 mm) or even smaller. Such anchors 526 may measure about 6 mm or more in their widest dimension. In some embodiments, housing 522 may have a diametrical dimension ("d") and anchor 526 may have a diametrical dimension ("D") in the deployed state, and the ratio of D to d may be at least about 3.5. In other embodiments, the ratio of D to d may be at least about 4.4, and more preferably at least about 7, and even more preferably at least about 8.8. These are only examples, however, and other larger or smaller anchors 526 may be disposed within a larger or smaller housing 522. The dimensions of an anchor may vary depending on the particular usage. For example, anchors used for ventriculoplasty may permit the use of larger anchors than those used for annuloplasty due to fewer space constraints in the main compartment of the ventricles than in the subvalvular spaces. Furthermore, any convenient number of anchors 526 may be disposed within housing 522. In one variation, for example, housing 522 may hold about 1 to about 20 anchors 526, and more preferably about 3 to about 10 anchors 526. Other variations may hold more anchors 526.

Anchor contacting member 530 and pull cord 532 may have any suitable configuration and may be manufactured from any material or combination of materials. In alternative embodiments of the invention, contacting member 530 may be pushed by a pusher member to contact and deploy anchors 526. Alternatively, any of the anchor deployment devices and methods previously described may be used.

Tether 534, as shown in FIG. 10, may comprise any of the tethers 534 or tether-like devices already described above, or any other suitable device. Tether 534 is generally attached to a distal-most anchor 526 at an attachment point 536. The attachment itself may be achieved via a knot, weld, adhesive, or by any other suitable attachment mechanism. Tether 234 then extends through an eyelet, loop or other similar configuration on each of the anchors 526 so as to be slidably coupled with the anchors 526. In the particular embodiment shown, tether 534 exits each aperture 528, then enters the next-most-proximal aperture, passes slidably through a loop on an anchor 526, and exits the same aperture 528. By entering and exiting each aperture 528, tether 534 allows the plurality of anchors 526 to be deployed into tissue and cinched. Alternate embodiments of housing 522, anchors 526 and tether 534 may also be used. For example, housing 522 may include a longitudinal slit through which tether 534 may pass, thus allowing tether 534 to reside wholly within housing before deployment.

Figure 11:
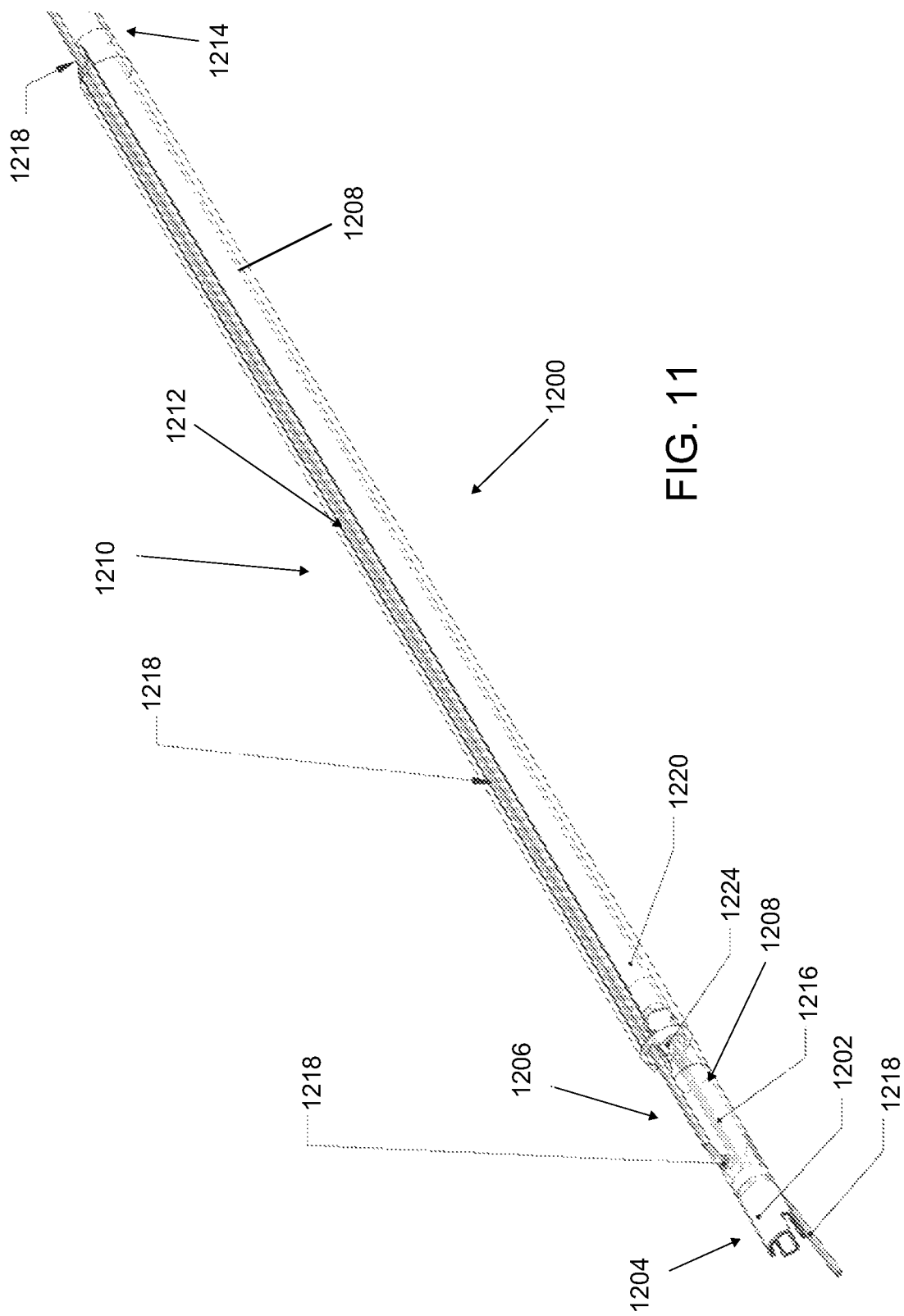
FIG. 11 is a perspective view of another embodiment of a delivery catheter.
Figure 15C:
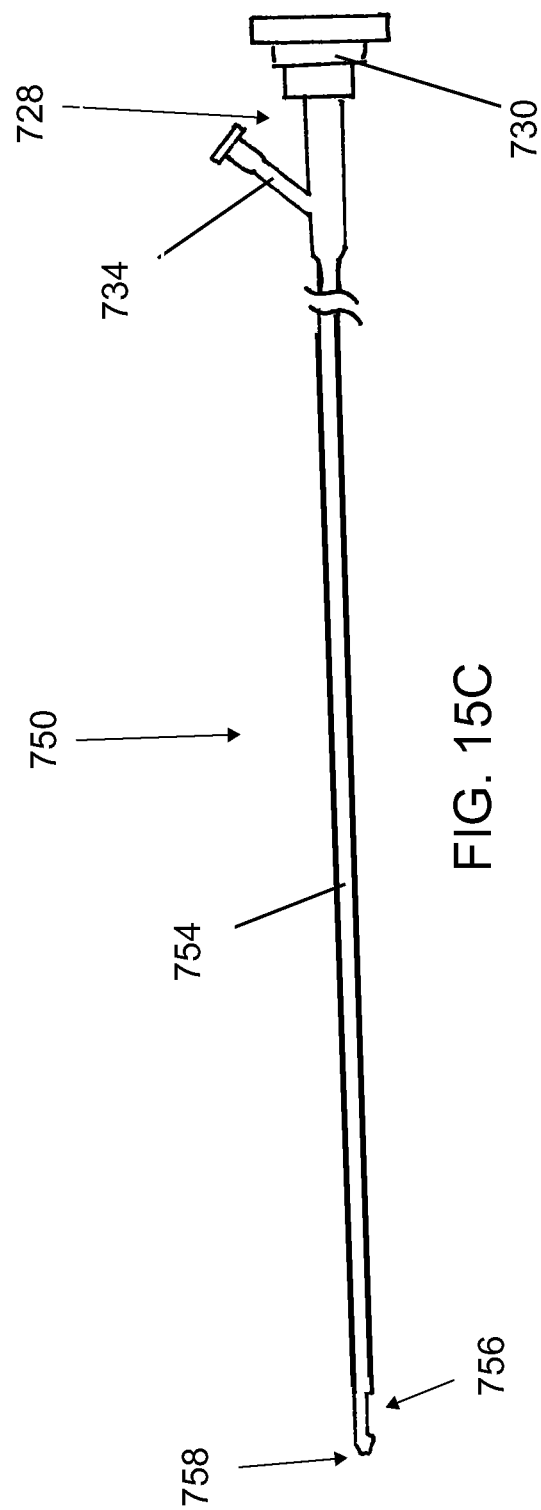
FIG. 15C illustrates one embodiment of an inner guide tunnel usable with the multi-opening guide tunnel of FIG. 15A.
Figure 15D:
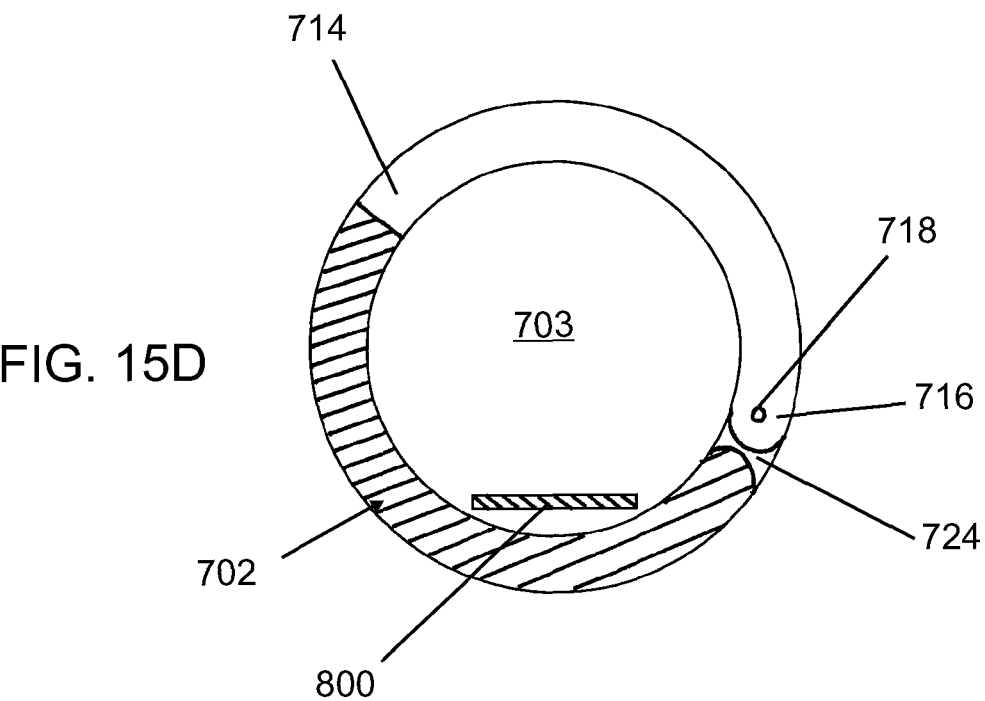
FIGS. 15D and 15E are schematic cross-sectional views of the multi-opening guide tunnel at various locations.
Figure 15E:
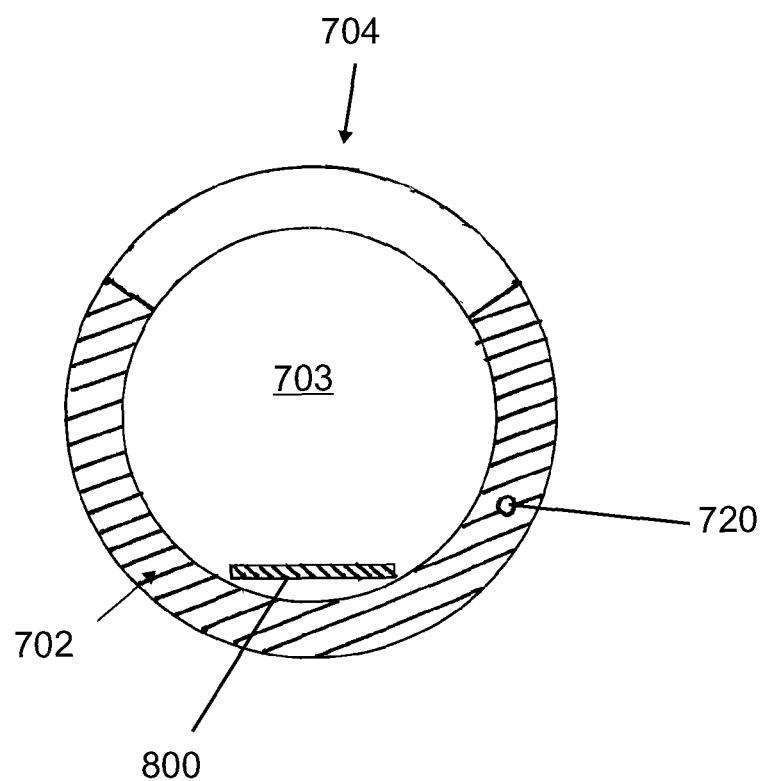

FIGS. 11 to 14 represent various views of one embodiment of a delivery catheter 1200 that can be used to deliver one or more anchors to a target site. As shown in FIG. 11, delivery catheter 1200 has a distal region 1204 including a tip 1202, an anchor-holding region 1206 including a primary lumen 1208, an intermediate region 1210 including both primary lumen 1208 and a secondary lumen 1212, and a proximal region 1214 including primary lumen 1208. An anchor 1216 is disposed within primary lumen 1208, in the anchor-holding region 1206. While only one anchor is shown in the anchor-holding region of this embodiment, in other embodiments of the invention, the delivery catheters may include an anchor-holding region that is adapted to hold multiple anchors. Similarly, while the variation shown in FIGS. 11 to 14 depict anchors adapted to be deployed from distal region 1204 of delivery catheter 1200, it should be understood that the anchors may be deployed from any suitable region of delivery catheter 1200, as desirable. For example, if desirable, the anchor may be delivered out of a side port or hole on the delivery catheter.

As shown in FIGS. 11 to 14, a tether 1218 may be threaded into a slot 1219 of tip 1202 (shown in FIGS. 13 and 14), and through an eyelet 1226 of anchor 1216. After extending through eyelet 1226, tether 1218 exits primary lumen 1208, and extends along an exterior surface 1221 of delivery catheter 1200 for the remainder of the length of the anchor-holding region, as shown in FIG. 13. Tether 1218 then enters secondary lumen 1212, and extends through the length of secondary lumen 1212, exiting secondary lumen 1212 at an end of distal region 1214. An actuator 1220 is slidably disposed within primary lumen 1208, and can be used to push or deploy anchor 1216 out of the primary lumen 1208. Actuator 1220 is in the form of a pushable generally tubular member, although other forms of actuators may be used. For example, in some variations, a solid rod may be used as an actuator. Once a sufficient distal portion of anchor 1216 has been displaced out of primary lumen 1208, the self-expanding properties of anchor 1216 may cause the biased distal ends to expand outwardly and cause the remainder of anchor 1216 to "spring out" or "shoot out" of distal end 1202 and facilitate tissue piercing by anchor 1216. Eyelet 1226 will also engage tether 1218 as anchor 1216 exits delivery catheter 1200. In other embodiments, actuator 1220 may be spring-loaded or biased to facilitate tissue piercing.

Delivery catheter 1200 may optionally comprise a retrieval member, such as a retrieval line or filament 1222 that is looped around eyelet 1226 of anchor 1216 and threaded proximally back through delivery catheter 1200. Retrieval filament 1222 is pulled of delivery catheter 1200 by eyelet 1226 when anchor 1216 is deployed. Retrieval filament 1222 may be used to pull back anchor 1216 into delivery catheter 1200 should anchor 1216 misfire and fail to engage body tissue. If anchor 1216 is successfully deployed, one end of retrieval filament 1222 may be pulled out from eyelet 1226 to release anchor 1216 from retrieval filament 1222.

Referring now to FIGS. 15A through 15E, in one embodiment of the invention, the guide tunnel 700 comprises a tubular body 702 with a central passageway 703 and multiple openings 704. Central passageway 703, depicted in FIGS. 15D and 15E, permits the insertion of a delivery catheter and the alignment of one or more retained anchors with one or more of the openings 704 of guide tunnel 700. Typically, openings 704 are grouped in a distal portion 706 of guide tunnel 700, but in other embodiments, openings 704 may be located more proximally. The lengths and configurations of the tubular body 702 and distal portion 706 may vary depending upon a variety of factors, including but not limited to the desired target location, such as the subannular groove region, and the access route, whether it is retrograde, antegrade, or requires a transseptal puncture. In one example, distal portion 706 of guide tunnel 700 comprises a flexible curved configuration. In some embodiments, openings 704 are preferably aligned along the greater curvature 708 of distal portion 706. In other embodiments, openings 704 may be aligned along the superior junction of the curved distal portion. Similarly, guide tunnel 700 may be configured for a cinchable implant inserted via the coronary sinus by aligning openings 704 along the lesser curvature 710 of distal portion 706. Distal portion 706 may optionally comprise an atraumatic tip, such as an inflatable balloon or a tapered tip 709 comprising a material with a low durometer. Guide tunnel 700 may be used in conjunction with a guide catheter to facilitate positioning of a delivery catheter at the desired anchoring sites.

In some embodiments, the openings 704 are arranged in a linear configuration along a longitudinal length of guide tunnel 700. Although openings 704 are depicted in FIG. 15A through 15E as having uniform dimensions, shapes, uniform spacing and angular and linear alignment, these and other features of guide tunnel 700 may be varied as desired. For example, if the cinchable implant comprises anchors of different sizes and anchor spacings, the anchor opening cross-sectional shapes and areas and relative spacing may be designed accordingly. For example, opening 704 of guide tunnel 700 has a generally semi-cylindrical shape (or rectangular shape when opening 704 is viewed orthogonally), while the aperture 528 of delivery device 520 in FIGS. 9 and 10 are generally oval in shape. In other examples, the openings of the guide tunnel may be squared, circular, semi-circular, triangular, octagonal, rhomboidal, trapezoidal, crescent-shaped, or any other shape. In still other examples, the openings may comprise slits which may deform to allow passage of an anchor or other component. The slits may have any of a variety of configurations, including linear, arcuate, cross or star-shaped configurations, for example.

In one embodiment of the invention, the retaining structures between anchor openings 704 may be configured to releasably retain the tether or coupling elements between the anchors. In a further embodiment, depicted in greater detail in FIGS. 16A through 16H, the retaining structures comprise latch structures 712 located between two adjacent openings 704 of guide tunnel 700. Referring back to FIG. 15B, which depicts latches 712 of guide tunnel 700 pulled away from tubular body 702, in some embodiments, latch 712 may comprise a base 714 and a free end 716. In some embodiments, latch 712 comprises a material and/or configuration to permit some deformation or deflection of latch 712 and for a tether or coupling member retained between two adjacent openings 704 to pass out of guide tunnel 700. Thus, in some embodiments, latch 712 comprises a flexible material, but in other embodiments, one or more latches may comprise a rigid material with a hinge joint or other type of joint that permits latch movement. The edges or corners of the latch structures 712 and/or openings 704 may be angled, as depicted in FIG. 14, or may be rounded.

Referring to FIG. 16B, latch 712 may be configured to permit control of the retention and/or release of the tether between deployed anchors. In some embodiments, latch 712 comprises a lumen 718 that is alignable with complementary segments 720 of a lumen located in the wall of the tubular body 702. The complementary lumen segments 720 may be provided in a notched region 724 which is complementary to free end 716 of latch 712. When aligned, each adjacent lumen 718 and segment of the longitudinal lumen 720 permits the insertion of a locking element 722. Locking element 722 can releasably secure the latch 712 in the notched region 724 by maintaining the alignment between the lumen 718 of latch 712 and lumen segment 720 of tubular body 702, thereby restricting the passage of a coupling member. When anchors are deployed through openings 704 adjacent to latch 712, the tether will be retained by latch 712.

In some embodiments, locking element 722 may have an elongate configuration and comprise a wire thread, or ribbon formed from metal, polymer, or combination thereof. Referring back to the embodiment depicted in FIG. 15A, latch 712 comprise transverse through-lumens 718 that complement the lumen segments of the longitudinal lumen 720 of the tubular body 702, but the particular orientations of the lumens or locking elements may vary, depending on the desired orientation of openings 704. Lumen 718 of latch 712 need not be a through-lumen or a transversely oriented lumen with respect to base 714 and free end 716 of latch 712. In some embodiments, latches 712 may comprise radio-opaque material to facilitate the positioning of a delivery catheter with respect to guide tunnel 700. In other embodiments, radio-opaque material may be located in or on tubular body 702 in angular position generally opposite one or more latches 712 or elsewhere.

In some embodiments, latch 712 may not maintain the alignment of lumen 718 with its complementary lumens 720 once locking element 722 is removed. In these embodiments, reinsertion or rethreading of locking element 722 back into lumen 718 may not work in situ. In other embodiments, however, guide tunnel 700 may be constructed such that latch 712 is biased to an alignment position and locking element 722 may be reengaged to one or more lumens 718, 720.

In some embodiments, a single locking element 722 is provided and is insertable through all lumens 718 of latch 712 and complementary lumens 720 of tubular body 702, and the aggregate lumen path from lumens 718 and complementary lumens 720 is substantially linear or curvilinear. With these particular embodiments, release of latches 712 start with the distalmost latch and finish with the most proximal latch. Although FIG. 16B depicts an interlocking fit between locking element 722, lumen 718 and lumen segment 720, other retaining mechanisms may also be used.

Referring again to FIGS. 16A through 16H, a more detailed description of guide tunnel 700 is provided. FIG. 16A illustrates distal section 706 of guide tunnel 700. Distal section 706 is configured with a curvature configured to facilitate the placement of anchors in the subannular groove region. Seven openings 706 are provided along the greater curvature 708 of distal section 706. In other embodiments, the number of openings 706 may vary from about 2 or about 3, to about 30 or more. In preferred embodiments, openings 706 may number from about 5 to about 20, while in most preferred embodiments, openings 706 may number from about 7 to about 10. In some embodiments, openings 706 may have a length of about 3 mm to about 20 mm, preferably about 5 mm to 10 mm and most preferably about 7 mm to about 8 mm. In some embodiments, openings 706 may have a width of about 1 mm to about 10 mm, preferably about 2 mm to about 7 mm, and most preferably about 3 mm to about 5 mm.

Referring back to FIG. 15A, proximally, guide tunnel 700 may comprise one or more access ports. One or more of the ports 728, for example, may also be configured with a hemostatic seal to reduce blood loss during the procedure, and or with a reversible locking mechanism 730 to maintain the relative position between an inserted component and guide tunnel 700. Port 728 may be used for insertion and removal of the delivery catheter, for example. In some embodiments, one or more ports 732, 734 may be provided to obtain blood samples, for injection of radiographic or therapeutic agents, or for the attachment of a pressure transducer. Another port 736 may be provided for manipulation of locking element 722 which controls the release of latch structures 712. In some embodiments, guide tunnel 700 may be used in conjunction with a delivery catheter comprising multiple anchors with preset spacing, similar to that depicted in FIGS. 9 and 10. In further embodiments, the spacing of the delivery catheter may match the spacing of openings 704 of guide tunnel 700. This particular combination may permit simultaneous deployment of anchors or reduce the time spent to align the delivery catheter and guide tunnel 700. In a preferred embodiment, a delivery catheter with plural anchors and a guide tunnel with plural openings may be provided in a kit with one or more other components described herein.

In another embodiment, guide tunnel 700 further comprises an inner guide tunnel 750 that is reversibly insertable into passageway 703 of guide tunnel 700. In these and other embodiments comprising inner guide tunnel 750, port 728 that is configured to receive the delivery catheter will be located on the inner guide tunnel 750 while guide tunnel 700 will have a port 752 configured to receive the inner guide tunnel 750. Inner guide tunnel 750 further comprises an inner tubular body 754 with one or more openings 756 located at the distal end 758 of the inner tubular body 754. Opening 756 may be configured with flanking or other configuration of radio-opaque markers that can be used to align opening 756 of inner guide tunnel 750 with the corresponding radio-opaque markers of latches 712. Opening 756 may comprise the same material as inner tubular body 754. In other embodiments, opening 756 is reinforced with a frame 806. In some embodiments, frame 806 may comprise a polymer of higher durometer than material comprising inner tubular body 754. In other embodiments, frame 806 may comprise a metal such as stainless steel, cobalt chromium, platinum-iridium, or Nitinol. In further embodiments, frame 806 may be plated with an additional metal, including but not limited to gold. In some embodiments, frame 806 is plated with additional material to alter its radio-opacity. Inner guide tunnel 750 may also be configured with one or other proximal ports 734 previously mentioned.

In some embodiments of the invention, guide tunnel 700, inner guide tunnel 750 or the delivery catheter may include a position sensor system to detect the relative position of inner guide tunnel 750 and/or the delivery catheter. In one embodiment, the position sensor system comprises a series of electrical contact points along passageway 703 of guide tunnel 700 that can form an electrical circuit with one or more electrical contact points located on inner tubular body 754. Similarly, electrical contact points in the lumen of inner guide tunnel 750 can be used to detect the position of delivery catheters inserted therein. The position sensor system may be used as a substitute or in conjunction with radio-opaque markers to facilitate alignment of various components. Other types of position sensor system are also contemplated, including but not limited to optical and magnetic detection mechanisms.

In some embodiments of the invention, guide tunnel 700 with inner guide tunnel 750 may be used with delivery catheters comprising a single anchor, or delivery catheters with multiple anchors. In these embodiments, inner guide tunnel 750 may be used to simplify positioning of delivery catheters with respect to openings 704 on guide catheter 700. Inner guide tunnel 750 may also be provided with one or more visual markings, detents, servo motor controlled positioning or other mechanisms to facilitate anchor delivery through openings 704. In some embodiments, inner guide tunnel 750 may be configured, for example, to reorient end-firing anchor delivery catheters to deploy anchors through the side openings 705 of guide tunnel 700.

In some embodiments, guide tunnel 700 and inner guide tunnel 750 may be configured to restrict or limit any rotational movement between the two components. Such a feature may be useful when positioning in more difficult target locations in the body that require considerable length, angulation and torque to reach that may result in rotation and/or length misalignment. In one embodiment of the invention, depicted in FIGS. 16C to 16E, passageway 703 of distal section 706 is configured with a rail 800, groove or other alignment structure to resist rotational movement of inner guide tunnel 750. Rail 800 is attached at a distal end 804 and a proximal end (not shown) and permits inner guide tunnel 750 to longitudinally slide along between its two attachment points, where rail 800 passes through slots 802 or slits formed in the tubular body 754 of inner guide tunnel 750. In some embodiments, the rail has a width to thickness ratio of about 5:1 to about 20:1, preferably about 8:1 to about 16:1, and most preferably about 9:1 to about 14:1. In other embodiments, rail 800 is not attached proximally and permits inner guide tunnel 750 to be fully withdrawn from guide tunnel 700 and exchanged for a different inner guide tunnel 750. Rail 800 preferably comprises materials selected to reduce or minimize any friction or cohesion effects between the rail and the material comprising tubular body 754 of inner guide tunnel 750. In some embodiments, rail 800 may comprise a metal such as stainless steel or Nitinol. In other embodiments, rail 800 or other alignment configuration may comprise a lubricious coating such as PTFE to reduce movement resistance of inner guide tunnel 750. In still other embodiments of the invention, rail 800 may have a different cross sectional shape from flat band configuration depicted in FIG. 14C, including but not limited to square, rectangle, circle, oval or other geometric shape.

In the embodiments of the cinchable implants described above, several embodiments of guide tunnel 700 or tunnel catheter 148 depict a single, longitudinal arrangement of alternating identical sized openings 154 and identical retaining elements or latches 712, but alternate configurations are also contemplated.

In some other embodiments, as depicted in FIGS. 17A to 17J, the guide tunnel 1000 may comprise a tubular body 1002 with a distal section 1004. The distal section 1004 may comprise a proximal curve 1006 and a distal curve 1008 extending distally from the proximal curve. The proximal curve 1006 may have an angle from about 1° to about 179°, for example, 90°. The distal section 1004 may be angled by the proximal curve 1006 such that it is substantially perpendicular to the tubular body 1002, e.g., may extend perpendicularly away from the plane of the depicted view. The distal curve 1008 may curve through various angles in multiple planes, and in some variations, may be a portion of a circular spiral. The spiral may comprise a right-handed, left-handed or more other spiral configuration. FIG. 17E depicts the guide tunnel 1000 from FIG. 17A rotated such that the distal curve is substantially co-planar with the plane of the depicted view. The diameter D4 of the distal curve may be from about 1.5 in to about 4 in, e.g., 2.75 in, or 3.25 in. The proximal section 1001 of the guide tunnel 1000 may have any number of ports, valves, etc. in a suitable arrangement for advancing guidewires, devices, flush agents, contrast agents, etc., as previously described.

FIG. 17B is a detailed view of the region of the distal section 1004 marked in FIG. 17A. An enlarged side view of the distal section 1004 taken from FIG. 17E is depicted in FIG. 17F. A superior perspective view of the distal section 1004 is also depicted in FIG. 17H. As described previously, the distal section 1004 may have one or more openings 1010 and one or more latches 1011 between each of the openings 1010. The distal section 1004 may have any number of openings 1010, for example, it may have 6, 7, 8, 9, 10, 11, 12, 15, 20, etc. openings. An inner guide tunnel 1012 may be provided through the lumen of tubular body 1002, and may extend into the lumen of the distal section 1004. The distal portion of the inner guide tunnel 1012 may comprise a distal tip valve 1016 and a window 1017. The distal tip valve 1016 may prevent the exchange of fluids when in a closed configuration, and may permit the passage of a guidewire when in an open configuration. For example, the distal tip valve 1016 may be a pliable material with thin slits. In the closed configuration, the thin slits are not parted, and may prevent liquids (such as contrast agents or perfusion solutions) from exiting the distal tip. When the inner guide tunnel 1012 is passed over a guidewire, the guidewire parts the pliable flexible valve material so that it may pass through. Once the guidewire is withdrawn or removed from the inner guide tunnel 1012, the distal tip valve 1016 assumes its closed configuration again.

The opening of the inner guide tunnel window 1017 may be further shaped by a contrast director 1018. The contrast director may be made of a flexible, pliable material and may have a slot 1020 that is shaped to direct the infusion of contrast agent to a desired region. The shape of the slot 1020 may also be configured to receive and to conform to the shape of any catheter or other instrument inserted through slot 1020, e.g. an anchor delivery catheter. Thus the contrast director may facilitate fluoroscopic or ultrasound viewing of the surrounding anatomy during anchor delivery, or to infuse one or more treatment agents to the region. For example, as shown in FIG. 17C, the slot may have an elongate proximal portion and a wider distal portion. The elongate proximal portion may be suitable for accommodating an anchor delivery catheter therethrough, while the wider distal portion may permit an effective quantity of contrast agent to be applied at the delivery site.

FIG. 17D depicts a cross-section of the tubular body 1002 taken along the lines 17D-17D. The inner guide tunnel 1012 is enclosed within the tubular body 1002. The tubular body 1002 may have a wire lumen 1003. The wire lumen 1003 may have a constant diameter along the length of the tubular body, or may be tapered towards the proximal and/or distal ends of the tubular body 1002. These tapered portions may help to position and/or stabilize a wire inserted in the lumen 1003 as the guide tunnel is advanced to the target location.

FIG. 17G depicts a cross-section of the distal curve 1008 taken along the lines 17G-17G. A portion of the outer shaft is cut away to form the window 1010, while the inner guide tunnel 1012 and the wire lumen 1003 remain intact. The angle A4 may be from about 10° to about 180°, e.g., about 45°.

In some variations, the distal-most window on a distal curve 1008 may be configured to help precisely position and deploy a pair of anchors, e.g., the two distal-most anchors of an anchor assembly. For example, as illustrated in FIGS. 17C, 17F, and 17I to 17K, a distal window segment 1014 may comprise a distal pairing feature 1022 configured to help ensure a certain spacing between the two distal-most anchors. The distal pairing feature 1022 may be used to facilitate delivery of two or more anchors in closer proximity to each other than the other windows of the guide tunnel. The distal pairing feature 1022 may comprise a proximal flap 1024, a middle flap 1026, and a distal flap 1028 that may be interleaved with each other. The flaps 1024, 1026, and 1028 may be made of a flexible, elastic, resilient material, e.g., any of a variety of silicones such as NuSil Med-4035, Med-4820, and MED50-5338, etc. The distal pairing feature 1022 may partition the window of the distal window segment 1014 into a distal window portion 1030 and a proximal window portion 1032. The position of the inner guide tunnel 1012 within the guide tunnel may be adjusted to align the slot 1020 with either the distal window portion 1030 or the proximal window portion 1032. The proximal-most window of the guide tunnel may also have one or more the components of the distal window segment to help position the proximal-most pair of anchors for deployment. In some variations, the proximal-most window may not have any latches or pairing features.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. An anchor for securing a tether to cardiac tissue, the anchor comprising:

a self-expanding, shape memory wire body having an unconstrained elongate form with a central curved segment having two ends, two straight segments connected to the two ends of the central curved segment, and two legs extending from the two straight segments, wherein the two legs cross each other at a crossover point, and wherein a loop region is defined between an apex of the central curved segment and the crossover point, wherein the distal tips of each leg, in an unconstrained configuration, point away from each other and the loop region has a height that is about 2 to about 6 times a width of the loop region.

2. The anchor of claim 1, wherein the anchor is made of a nickel titanium alloy.

3. The anchor of claim 1, wherein the height of the loop region is from about 0.07 inch to about 0.2 inch, and the width of the loop region is from about 0.03 inch to about 0.08 inch.

4. The anchor of claim 3, wherein the height of the loop region is about 0.173 inch and the width is about 0.061 inch.

* * * * *